United States Patent [19]

Ferrera et al.

[11] Patent Number: 6,159,165
[45] Date of Patent: *Dec. 12, 2000

[54] THREE DIMENSIONAL SPHERICAL MICRO-COILS MANUFACTURED FROM RADIOPAQUE NICKEL-TITANIUM MICROSTRAND

[75] Inventors: David A. Ferrera, San Francisco; Christopher G. M. Ken, San Mateo, both of Calif.

[73] Assignee: Micrus Corporation, Mountain View, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 09/019,841

[22] Filed: Feb. 6, 1998

Related U.S. Application Data

[63] Continuation-in-part of application No. 08/986,004, Dec. 5, 1997, abandoned.

[51] Int. Cl.[7] ........................................ A61B 5/00
[52] U.S. Cl. .................... 600/585; 606/194; 606/191
[58] Field of Search ...................... 600/434, 435, 600/585; 606/191, 108, 200, 194; 604/52, 57

[56] References Cited

U.S. PATENT DOCUMENTS

| | | | |
|---|---|---|---|
| 1,341,052 | 5/1920 | Gale . | |
| 1,667,730 | 5/1928 | Green ............................................ | 75/84 |
| 2,078,182 | 4/1937 | MacFarland ................................. | 75/84 |
| 2,549,335 | 4/1951 | Rahthus ....................................... | 59/83 |
| 3,334,629 | 8/1967 | Cohn ........................................ | 128/325 |
| 3,452,742 | 7/1969 | Muller ........................................ | 128/2 |
| 3,485,234 | 12/1969 | Stevens ....................................... | 128/2 |
| 3,649,224 | 3/1972 | Anderson et al. ....................... | 29/182.5 |
| 3,868,956 | 3/1975 | Alfidi et al. ............................. | 128/345 |
| 4,161,952 | 7/1979 | Kinney et al. ............................ | 128/786 |

(List continued on next page.)

FOREIGN PATENT DOCUMENTS

| | | |
|---|---|---|
| 0 183372 A1 | 6/1986 | European Pat. Off. . |
| 0 278 937 A2 | 8/1988 | European Pat. Off. . |
| 0 382014 A1 | 8/1990 | European Pat. Off. . |
| 0 518 704 A1 | 12/1992 | European Pat. Off. . |
| 0 627 201 A1 | 12/1994 | European Pat. Off. . |

(List continued on next page.)

OTHER PUBLICATIONS

Christos A. Athanasoulis, M.D. The New England Journal Of Medicine, May 15, 1980 "Therapeutic Applications of Angiography" pp.1117–1125 (1 of 2).

Christos A. Athanasoulis, M.D. The New England Journal Of Medicine, May 22, 1980 "Therapeutic Applications of Angiography" pp. 1174–1179 (2 of 2).

(List continued on next page.)

*Primary Examiner*—Cary O'Connor
*Assistant Examiner*—Charles Marmor, II
*Attorney, Agent, or Firm*—Fulwider Patton Lee & Utecht, LLP

[57] ABSTRACT

The three dimensional device is adapted to be inserted into a portion of a vasculature for occluding the portion of the vasculature for use in interventional therapy and vascular surgery. The device is formed from a multi-stranded micro-cable having a plurality of flexible strands of a shape memory material and at least one radiopaque strand. The flexible strands in a multi-stranded micro-cable of the device can be helically wound, or can be configured as parallel, longitudinal strands, and can also be formed to have a secondary, three dimensional therapeutic configuration, such as helical, conical, spherical, or other geometric shapes. The strands can be made of a shape memory nickel titanium alloy, that is highly flexible at a temperature appropriate for introduction into the body via a catheter, and that after placement will take on the therapeutic shape. The device can also include a therapeutic agent, and can be bundled by an outer cover to constrain the strands of the micro-cable about a longitudinal axis to produce a composite banded cable.

163 Claims, 8 Drawing Sheets

U.S. PATENT DOCUMENTS

| | | | |
|---|---|---|---|
| 4,205,680 | 6/1980 | Marshall | 128/296 |
| 4,257,421 | 3/1981 | Beal | 128/348 |
| 4,494,531 | 1/1985 | Gianturco | 128/1 R |
| 4,512,338 | 4/1985 | Balko et al. | 128/1 R |
| 4,553,545 | 11/1985 | Maass et al. | 128/341 |
| 4,580,568 | 4/1986 | Gianturco | 128/345 |
| 4,629,458 | 12/1986 | Pinchuk | 623/1 |
| 4,638,803 | 1/1987 | Rand | 128/325 |
| 4,655,771 | 4/1987 | Wallsten | 623/1 |
| 4,670,286 | 6/1987 | Nyilas et al. | 427/2 |
| 4,682,607 | 7/1987 | Vaillancourt et al. | 600/585 |
| 4,718,907 | 1/1988 | Karwoski et al. | 623/12 |
| 4,748,986 | 6/1988 | Morrison et al. | 600/585 |
| 4,768,507 | 9/1988 | Fischell et al. | 128/303 R |
| 4,795,458 | 1/1989 | Regan | 623/1 |
| 4,795,741 | 1/1989 | Leshchiner et al. | 514/21 |
| 4,798,606 | 1/1989 | Pinchuk | 623/1 |
| 4,800,882 | 1/1989 | Gianturco | 128/343 |
| 4,813,925 | 3/1989 | Anderson, Jr. et al. | 604/8 |
| 4,820,298 | 4/1989 | Leveen et al. | 623/1 |
| 4,830,003 | 5/1989 | Wolff et al. | 128/343 |
| 4,850,960 | 7/1989 | Grayzel | 604/53 |
| 4,856,516 | 8/1989 | Hillstead | 128/343 |
| 4,922,924 | 5/1990 | Gambale et al. | 600/585 |
| 4,932,419 | 6/1990 | de Toledo | 600/585 |
| 4,950,258 | 8/1990 | Kawai et al. | 604/281 |
| 4,954,126 | 9/1990 | Wallsten | 600/36 |
| 4,957,479 | 9/1990 | Roemer | 604/8 |
| 4,957,501 | 9/1990 | Lahille et al. | 606/200 |
| 4,990,155 | 2/1991 | Wilkoff | 606/191 |
| 4,994,069 | 2/1991 | Ritchart et al. | 606/191 |
| 4,998,916 | 3/1991 | Hammerslag et al. | 604/95 |
| 5,019,090 | 5/1991 | Pinchuk | 606/194 |
| 5,025,799 | 6/1991 | Wilson | 600/585 |
| 5,026,377 | 6/1991 | Burton et al. | 606/108 |
| 5,037,377 | 8/1991 | Alonso | 600/36 |
| 5,037,391 | 8/1991 | Hammerslag et al. | 604/95 |
| 5,041,084 | 8/1991 | DeVries et al. | 604/43 |
| 5,055,101 | 10/1991 | McCoy | 604/95 |
| 5,061,275 | 10/1991 | Wallsten et al. | 623/1 |
| 5,063,935 | 11/1991 | Gambale | 600/434 |
| 5,064,435 | 11/1991 | Porter | 623/12 |
| 5,065,769 | 11/1991 | De Toledo | 128/772 |
| 5,071,407 | 12/1991 | Termin et al. | 604/104 |
| 5,092,847 | 3/1992 | Pozzo | 604/170 |
| 5,104,404 | 4/1992 | Wolff | 623/1 |
| 5,108,407 | 4/1992 | Geremia et al. | 606/108 |
| 5,111,829 | 5/1992 | De Toledo | 128/772 |
| 5,122,136 | 6/1992 | Guglielmi et al. | 606/32 |
| 5,129,890 | 7/1992 | Bates et al. | 604/281 |
| 5,133,731 | 7/1992 | Butler et al. | 606/191 |
| 5,133,732 | 7/1992 | Wiktor | 606/195 |
| 5,135,516 | 8/1992 | Sahatjian et al. | 604/265 |
| 5,139,243 | 8/1992 | Balsells | 267/167 |
| 5,141,502 | 8/1992 | Macaluso, Jr. | 604/281 |
| 5,143,085 | 9/1992 | Wilson | 128/772 |
| 5,147,370 | 9/1992 | McNamara et al. | 606/108 |
| 5,151,105 | 9/1992 | Kwan-Gett | 623/1 |
| 5,152,784 | 10/1992 | Tsilibary | 623/1 |
| 5,160,341 | 11/1992 | Brenneman et al. | 606/198 |
| 5,167,233 | 12/1992 | Eberle et al. | 128/662.06 |
| 5,171,273 | 12/1992 | Silver et al. | 623/13 |
| 5,174,302 | 12/1992 | Palmer | 600/585 |
| 5,176,625 | 1/1993 | Brisson | 604/8 |
| 5,176,661 | 1/1993 | Evard et al. | 604/282 |
| 5,183,085 | 2/1993 | Timmermans | 140/89 |
| 5,184,627 | 2/1993 | De Toledo | 128/772 |
| 5,186,992 | 2/1993 | Kite, III | 428/36.3 |
| 5,197,977 | 3/1993 | Hoffman, Jr. et al. | 623/1 |
| 5,203,772 | 4/1993 | Hammerslag et al. | 604/95 |
| 5,211,183 | 5/1993 | Wilson | 600/585 |
| 5,211,658 | 5/1993 | Clouse | 623/1 |
| 5,213,111 | 5/1993 | Cook et al. | 600/585 |
| 5,217,484 | 6/1993 | Marks | 606/200 |
| 5,222,969 | 6/1993 | Gillis | 606/194 |
| 5,226,911 | 7/1993 | Chee et al. | 606/191 |
| 5,228,453 | 7/1993 | Sepetka | 600/585 |
| 5,230,348 | 7/1993 | Ishibe et al. | 600/585 |
| 5,234,437 | 8/1993 | Sepetka | 606/108 |
| 5,234,456 | 8/1993 | Silvestrini | 606/194 |
| 5,238,004 | 8/1993 | Sahatjian et al. | 600/585 |
| 5,241,970 | 9/1993 | Johlin, Jr. et al. | 128/772 |
| 5,243,996 | 9/1993 | Hall | 600/585 |
| 5,246,014 | 9/1993 | Williams et al. | 607/122 |
| 5,250,071 | 10/1993 | Palermo | 606/198 |
| 5,251,640 | 10/1993 | Osborne | 600/585 |
| 5,253,653 | 10/1993 | Diagle et al. | 128/772 |
| 5,256,146 | 10/1993 | Ensminger et al. | 604/104 |
| 5,258,042 | 11/1993 | Mehta | 623/66 |
| 5,259,393 | 11/1993 | Corso, Jr. et al. | 600/585 |
| 5,303,714 | 4/1994 | Abele et al. | 128/772 |
| 5,304,121 | 4/1994 | Sahatjian | 604/53 |
| 5,304,194 | 4/1994 | Chee et al. | 606/191 |
| 5,312,415 | 5/1994 | Palermo | 606/108 |
| 5,336,205 | 8/1994 | Zenzen et al. | 604/280 |
| 5,341,818 | 8/1994 | Abrams et al. | 600/585 |
| 5,342,387 | 8/1994 | Summers | 606/198 |
| 5,350,397 | 9/1994 | Palermo et al. | 606/200 |
| 5,354,295 | 10/1994 | Guglielmi et al. | 606/32 |
| 5,356,388 | 10/1994 | Sepetka et al. | 604/164 |
| 5,368,049 | 11/1994 | Raman et al. | 600/585 |
| 5,373,856 | 12/1994 | Granouillet | 600/585 |
| 5,382,259 | 1/1995 | Phelps et al. | 606/151 |
| 5,386,828 | 2/1995 | Owens et al. | 600/585 |
| 5,409,015 | 4/1995 | Palermo | 600/585 |
| 5,413,597 | 5/1995 | Krajicek | 623/1 |
| 5,417,708 | 5/1995 | Hall et al. | 606/200 |
| 5,421,338 | 6/1995 | Crowley et al. | 128/662.06 |
| 5,423,829 | 6/1995 | Pham et al. | 606/108 |
| 5,423,849 | 6/1995 | Engelson et al. | 606/191 |
| 5,429,597 | 7/1995 | DeMello et al. | 604/49 |
| 5,437,282 | 8/1995 | Koger et al. | 128/662.06 |
| 5,439,485 | 8/1995 | Mar et al. | 607/119 |
| 5,441,516 | 8/1995 | Wang et al. | 606/198 |
| 5,443,478 | 8/1995 | Purdy | 606/200 |
| 5,460,187 | 10/1995 | Daigle et al. | 128/772 |
| 5,462,523 | 10/1995 | Samson et al. | 604/30 |
| 5,465,732 | 11/1995 | Abele | 128/772 |
| 5,514,115 | 5/1996 | Frantzen et al. | 604/281 |
| 5,514,128 | 5/1996 | Hillsman et al. | 600/585 |
| 5,514,176 | 5/1996 | Bosley, Jr. | 623/1 |
| 5,520,194 | 5/1996 | Miyata et al. | 600/585 |
| 5,522,819 | 6/1996 | Graves et al. | 606/113 |
| 5,522,822 | 6/1996 | Phelps et al. | 606/151 |
| 5,522,836 | 6/1996 | Palermo | 606/200 |
| 5,523,092 | 6/1996 | Hanson et al. | 424/423 |
| 5,527,338 | 6/1996 | Purdy | 606/200 |
| 5,527,354 | 6/1996 | Fontaine et al. | 623/1 |
| 5,531,715 | 7/1996 | Engelson et al. | 604/265 |
| 5,540,680 | 7/1996 | Guglielmi et al. | 606/32 |
| 5,540,701 | 7/1996 | Sharkey et al. | 606/153 |
| 5,540,713 | 7/1996 | Schnepp-Pesch et al. | 606/198 |
| 5,549,624 | 8/1996 | Mirigian et al. | 606/191 |
| 5,549,663 | 8/1996 | Cottone, Jr. | 623/1 |
| 5,562,641 | 10/1996 | Flomenblit et al. | 604/281 |
| 5,562,698 | 10/1996 | Parker | 606/200 |
| 5,569,245 | 10/1996 | Guglielmi et al. | 606/49 |
| 5,582,619 | 12/1996 | Ken | 606/191 |
| 5,601,593 | 2/1997 | Freitag | 606/198 |
| 5,603,694 | 2/1997 | Brown et al. | 604/49 |
| 5,607,445 | 3/1997 | Summers | 606/198 |
| 5,609,627 | 3/1997 | Goicoechea et al. | 623/1 |

| | | | |
|---|---|---|---|
| 5,618,301 | 4/1997 | Hauenstein et al. | 606/198 |
| 5,624,449 | 4/1997 | Pham et al. | 606/108 |
| 5,624,461 | 4/1997 | Mariant | 606/191 |
| 5,632,772 | 5/1997 | Alcime et al. | 623/1 |
| 5,637,113 | 6/1997 | Tartaglia et al. | 623/1 |
| 5,639,277 | 6/1997 | Mariant et al. | 606/191 |
| 5,643,254 | 7/1997 | Scheldrup et al. | 606/32 |
| 5,645,082 | 7/1997 | Sung et al. | 128/897 |
| 5,645,558 | 7/1997 | Horton | 606/191 |
| 5,649,949 | 7/1997 | Wallace et al. | 606/191 |
| 5,667,522 | 9/1997 | Flomenblit et al. | 606/198 |
| 5,669,931 | 9/1997 | Kupiecki et al. | 606/191 |
| 5,676,697 | 10/1997 | McDonald | 623/1 |
| 5,690,643 | 11/1997 | Wijay | 606/108 |
| 5,690,666 | 11/1997 | Berenstein et al. | 606/191 |
| 5,690,667 | 11/1997 | Gia | 606/191 |
| 5,690,671 | 11/1997 | Mcgurk et al. | 606/200 |
| 5,693,085 | 12/1997 | Buirge et al. | 623/1 |
| 5,700,258 | 12/1997 | Mirigian et al. | 606/1 |
| 5,718,711 | 2/1998 | Berenstein et al. | 606/191 |
| 5,733,329 | 3/1998 | Wallace et al. | 623/1 |
| 5,749,891 | 5/1998 | Ken et al. | 606/191 |
| 5,749,894 | 5/1998 | Engelson | 606/191 |
| 5,766,219 | 6/1998 | Horton | 606/191 |
| 5,800,511 | 9/1998 | Mayer | 623/1 |
| 5,800,525 | 9/1998 | Bachinski et al. | 606/200 |
| 5,814,062 | 9/1998 | Sepetka et al. | 606/198 |
| 5,817,100 | 10/1998 | Igaki | 606/108 |
| 5,843,118 | 12/1998 | Sepetka et al. | 606/194 |

FOREIGN PATENT DOCUMENTS

| | | |
|---|---|---|
| 0 743 047 A2 | 11/1996 | European Pat. Off. . |
| 0 747 014 A1 | 12/1996 | European Pat. Off. . |
| 0 820 726 A2 | 1/1998 | European Pat. Off. . |
| 592182 | 5/1925 | France . |
| 4102550 A1 | 8/1991 | Germany . |
| 197 04 269 A1 | 11/1997 | Germany . |
| 2 066 839 | 7/1981 | United Kingdom . |
| WO 92/14408 | 9/1992 | WIPO . |
| WO 94/09705 | 5/1994 | WIPO . |
| WO 94/10936 | 5/1994 | WIPO . |
| WO 94/16619 | 8/1994 | WIPO . |
| WO 94/16629 | 8/1994 | WIPO . |
| WO 95/18585 | 7/1995 | WIPO . |
| WO 95/21592 | 8/1995 | WIPO . |
| WO 97/26939 | 7/1997 | WIPO . |
| WO 97/31672 | 9/1997 | WIPO . |
| WO 97/48351 | 12/1997 | WIPO . |
| WO 99/05977 | 2/1999 | WIPO . |
| WO 99/07294 | 2/1999 | WIPO . |

OTHER PUBLICATIONS

Alex Berenstein, M.D. And Irvin I. Kricheff, M.D. "Catheter and Material Selection For Transarterial Embolization: Technical Considerations" Radiology, Sep. 1979; pp. 631–639.

O.A. Battista, et al. Journal of Applied Polymer Science 1967 "Colloidal Macromolecular Phenomena. Part II. Novel Microcrystals of Polymers" pp. 481–498.

Sadek K. Hilal, M.D. et al. Journal of Neurological Surgery "Therapeutic Percutaneous Embolization For Extra–Axial Vascular Lesions of the Head, Neck And Spine" Sep. 1975; pp. 275–287.

Stephen L. Kaufman, M.D. et al. Investigative Radiology, May–Jun. 1978 "Transcatheter Embolization With Microfibrillar Collagen in Swine"; pp. 200–204.

Ashok J. Kumar, et al., Journal of Neuroradiology (1982) "Preoperative Embolization of Hypervascular Head And Neck Neoplasms Using Microfibrillar Collagen", pp. 163–168.

Richard E. Latchaw, M.D. et al., Radiology (1979) "Polyvinyl Foam Embolization of Vascular And Neoplastic Lesions of the Head, Neck And Spine" pp. 669–679.

Stewart R. Reuter, M.D. et al. American Journal of Radiology, Sep. 1975 "Selective Arterial Embolization For Control Of Massive Upper Gastrointestinal Bleeding" pp. 119–126.

Glenn H. Roberson, et al., American Journal of Radiology, Oct. 1979 "Therapeutic Embolization of Juvenile Angiofibroma" pp. 657–663.

Sidney Wallace M.D. et al., Cancer, Oct. 1979 "Arterial Occlusion of Pelvic Bone Tumors"; pp. 322–325 & 661–663.

"Mechanical Devices For Arterial Occlusion" By C. Gianturco, M.D., et al., Jul. 1975 pp. 428–435.

"Therapeutic Vascular Occlusion Utilizing Steel Coil Technique: Clinical Applications" By Sidney Wallace, et al., Am J. Roentgenol (1976); pp. 381–387.

"Transcatheter Intravascular Coil Occlusion Of Experimental Arteriovenous Fistulas", By James H. Anderson, et al., Am. J. Roentgenol, Nov. 1977, pp. 795–798.

"'Mini' Gianturco Stainless Steel Coils For Transcatheter Vascular Occlusion" By James H. Anderson, et al., From The Department Of Diagnostic Radiology at the University Of Texas System Cancer Center, Aug. 1978, pp. 301–303.

"A New Improved Coil For Tapered–Tip Catheter For Arterial Occlusion" by Vincent P. Chuang, M.D., et al., May 1980, pp. 507–509.

"*Neurosurgery Interactive Aricle Part 2–Clincal Studies Embolization of Cerebral Arteriovenous Malformations: Part II–Aspects of Complications and Late Outcome*" by Christopher Lundqvist, M.D., Ph.D., G. Wilkolm, M.D., Ph.D., P. Svendsen, M.D., Ph.D., Sep. 1996, pp. 1–16.

"*Shape Memory Alloys*" by Jeff Perkins, pp. 1095–1096.

"*Treatment of Large and Giant Fusiform Intracranial Aneurysms with Guglielmi Detachable Coils*", by Y. Pierre Gobin, M.D., Et al., J. Neurosurg., Jan. 1996, pp. 55–62, vol. 84.

"*Endovascular Treatment of Basilar Tip Aneurysms Using Electrolytically Detachable Coils*", by Cameron G. McDougall, M.D., et al., J. Neurosurg., Mar. 1996, pp. 393–399, vol. 84.

"*Retrieval of Guglielmi Detachable Coil After Unraveling and Fracture: Case Report and Experimental Results*", by Scott C. Standard, M.D., et al., Neurosurgery, Nov. 1994, pp. 994–999, vol. 35, No. 5.

"*Catheters, Embolic Agents Spark Neurointervention*", by Gary Duckwiller, M.D., et al., Diagnostic Imaging, May 1994, pp. 66–70 & 102.

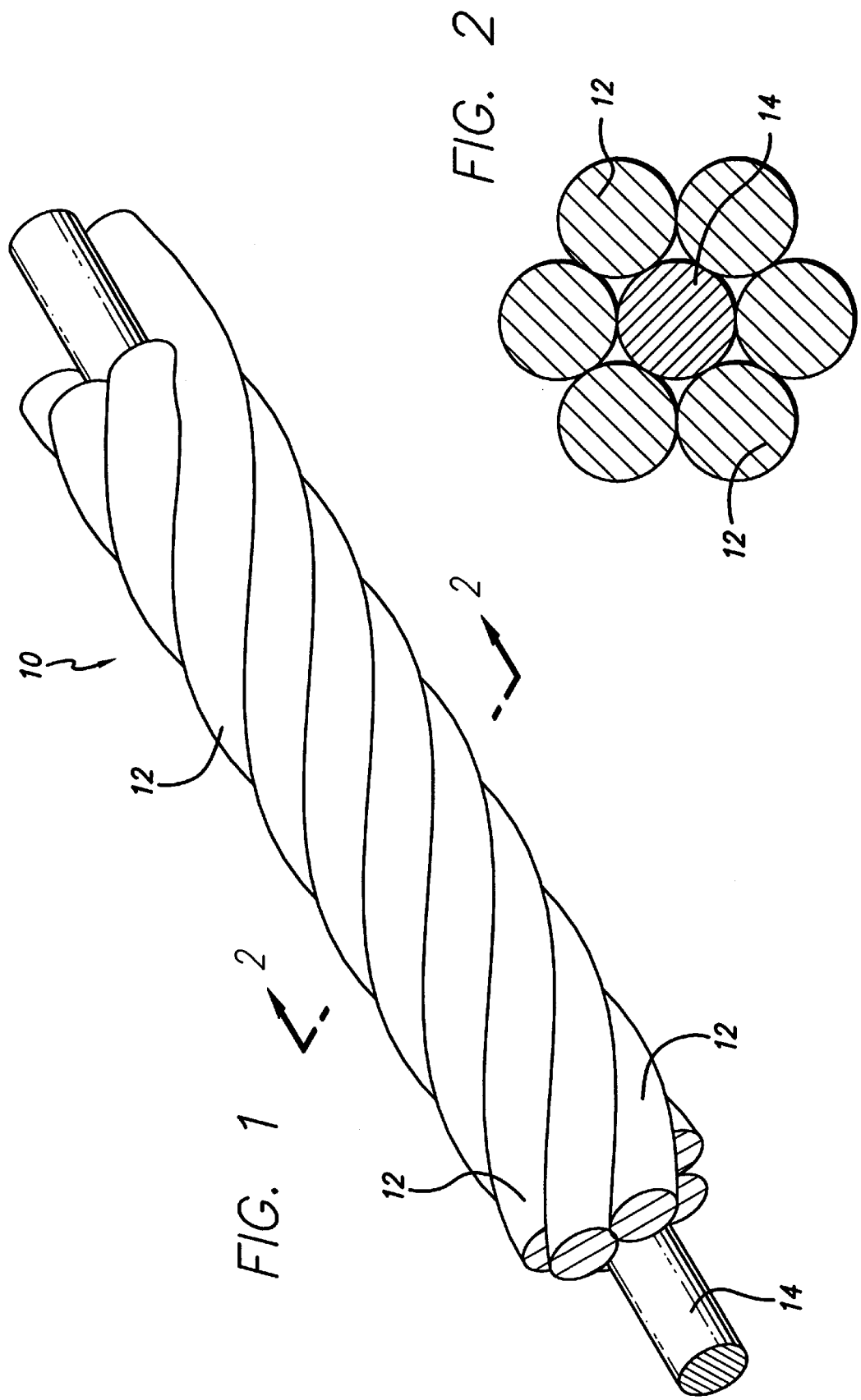

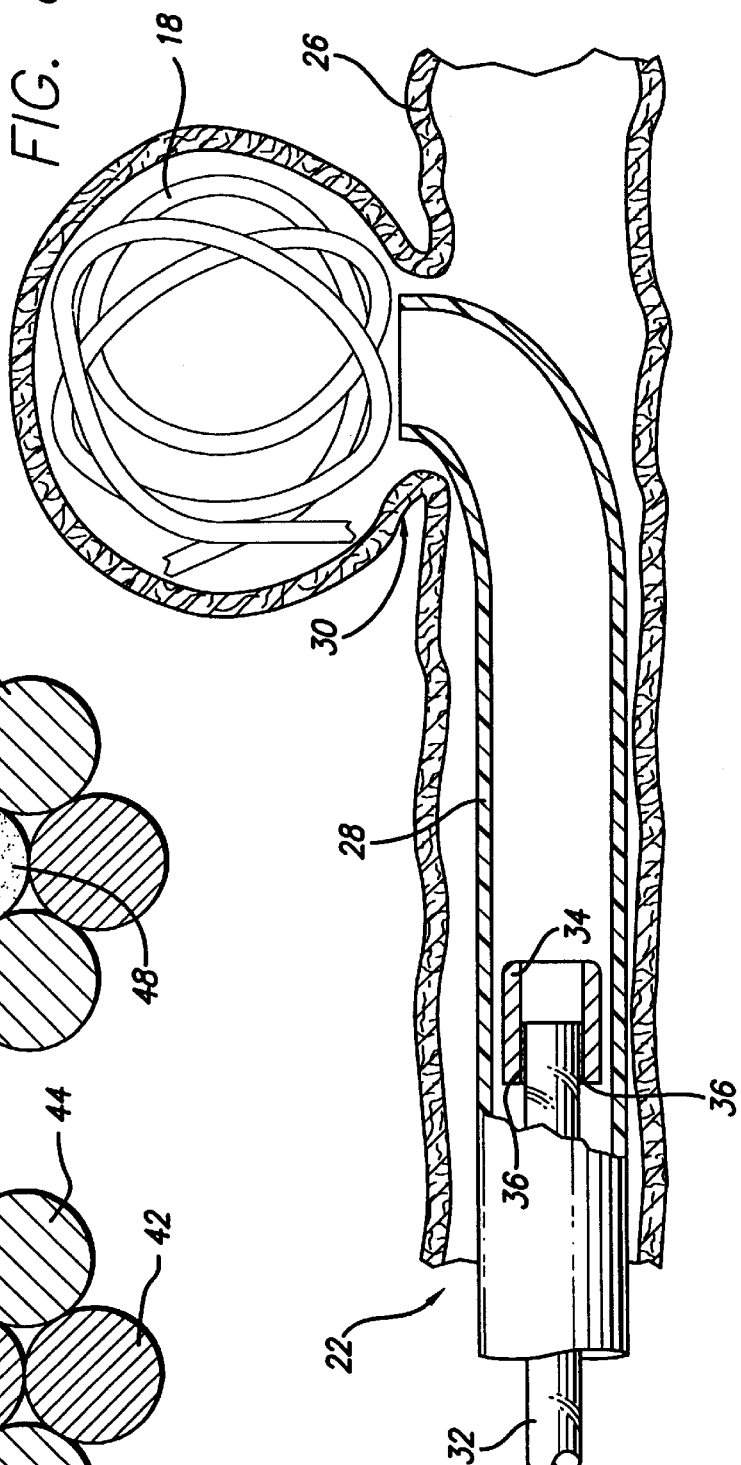

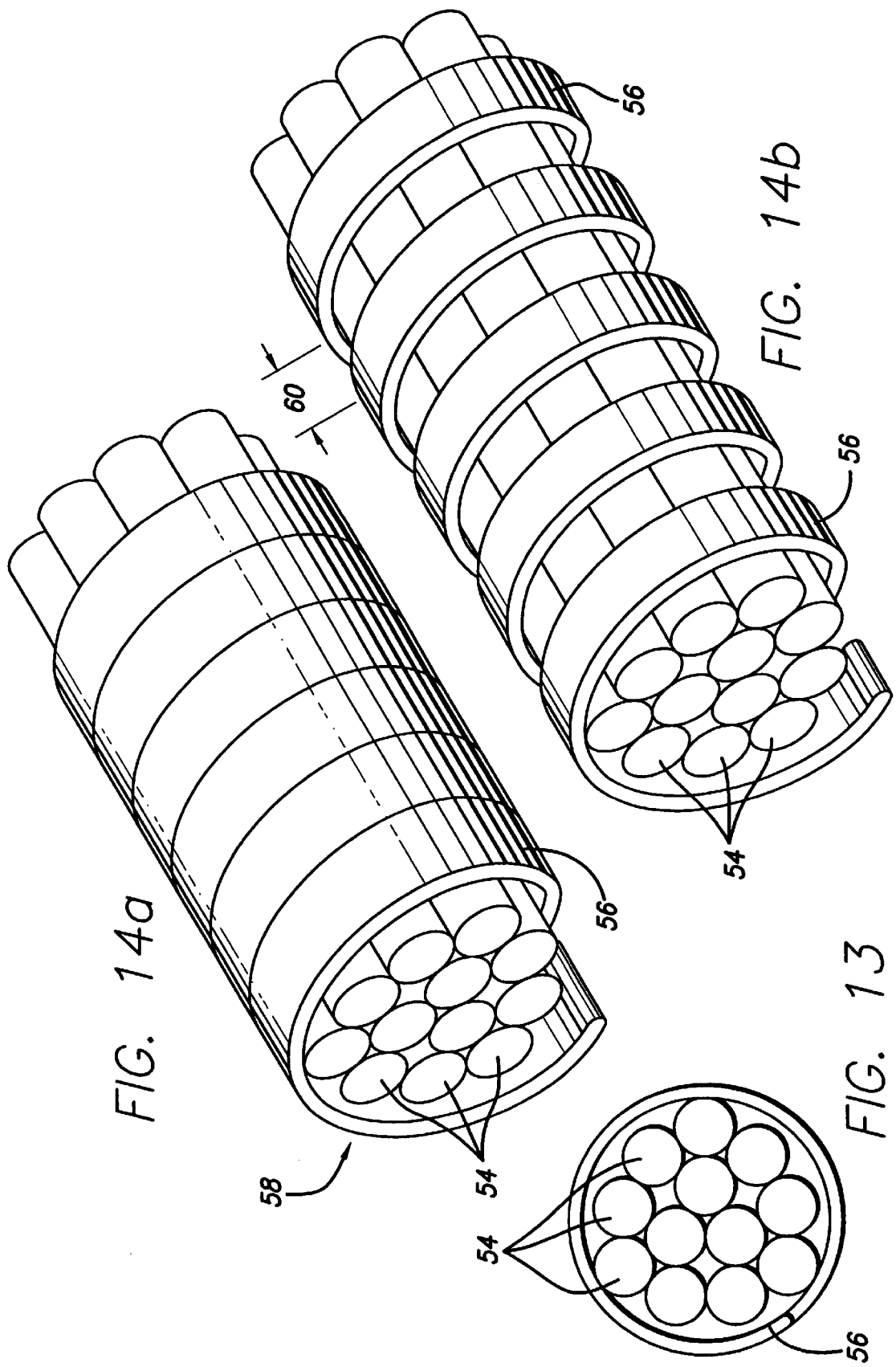

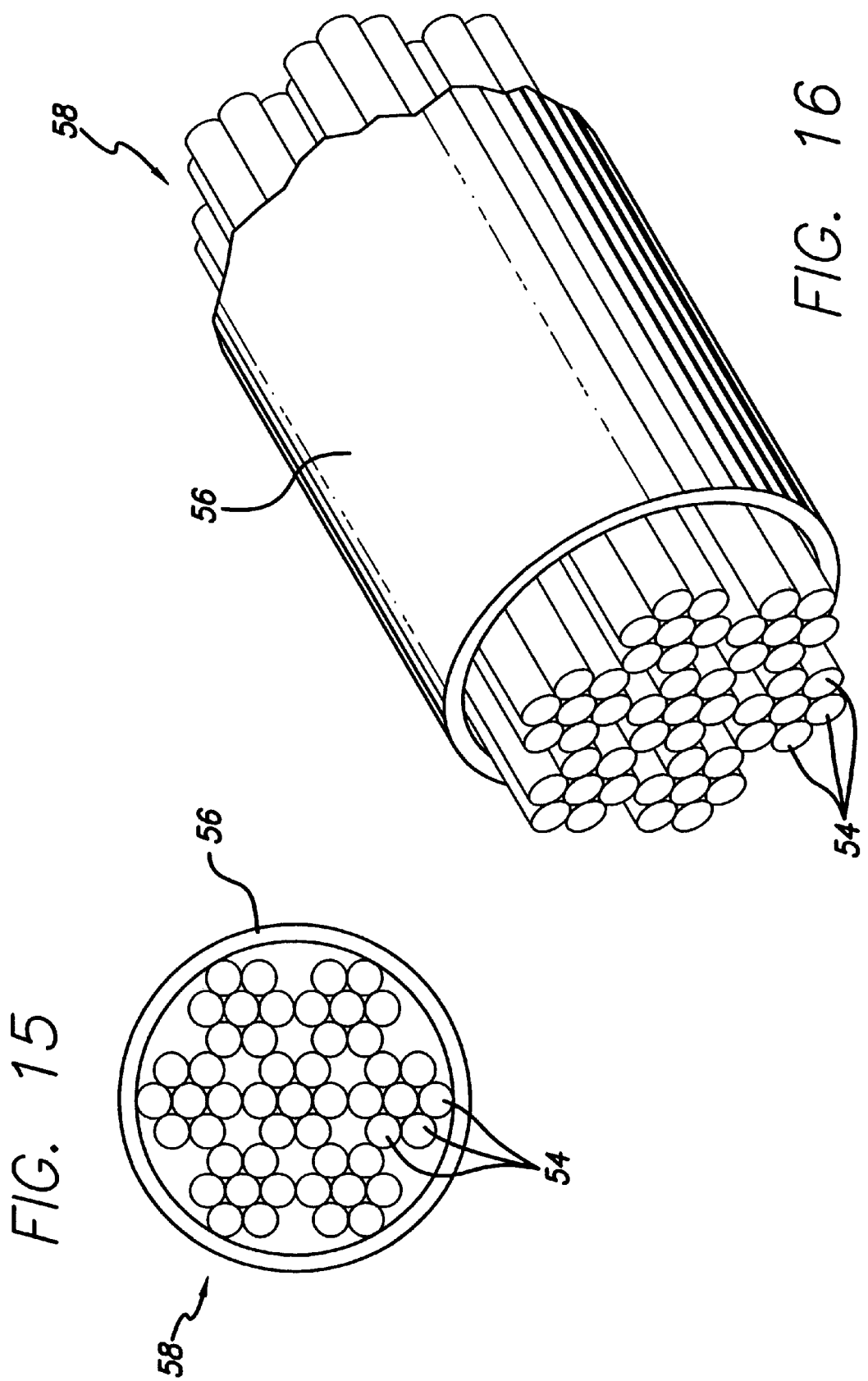

THREE DIMENSIONAL SPHERICAL MICRO-COILS MANUFACTURED FROM RADIOPAQUE NICKEL-TITANIUM MICROSTRAND

RELATED APPLICATIONS

This is a continuation-in-part of the co-pending application Ser. No. 08/986,004 by DAVID A. FERRERA and CHRISTOPHER KEN entitled "MICRO-STRAND CABLE WITH ENHANCED RADIOPACITY" filed Dec. 5, 1997, now abandoned.

BACKGROUND OF THE INVENTION

1. Field of the Invention

This invention relates generally to implantable devices for interventional therapeutic treatment or vascular surgery, and concerns a stranded micro-cable with enhanced radiopacity that can be used to fabricate a vascular device, a stent, a guidewire or the like. More particularly, the invention relates to three dimensional microcoil vasoocclusive devices fabricated from stranded micro-cable.

2. Description of Related Art

The art and science of interventional therapy and surgery has continually progressed towards treatment of internal defects and diseases by use of ever smaller incisions or access through the vasculature or body openings, in order to reduce the trauma to tissue surrounding the treatment site. One important aspect of such treatments involves the use of catheters to place therapeutic devices at a treatment site by access through the vasculature. Examples of such procedures include transluminal angioplasty, placement of stents to reinforce the walls of a blood vessel or the like and the use of vasoocclusive devices to treat defects in the vasculature. There is a constant drive by those practicing in the art to develop new and more capable systems for such applications. When coupled with developments in biological treatment capabilities, there is an expanding need for technologies that enhance the performance of interventional therapeutic devices and systems.

One specific field of interventional therapy that has been able to advantageously use recent developments in technology is the treatment of neurovascular defects. More specifically, as smaller and more capable structures and materials have been developed, treatment of vascular defects in the human brain which were previously untreatable or represented unacceptable risks via conventional surgery have become amenable to treatment. One type of non-surgical therapy that has become advantageous for the treatment of defects in the neurovasculature has been the placement by way of a catheter of vasoocclusive devices in a damaged portion of a vein or artery.

Vasoocclusion devices are therapeutic devices that are placed within the vasculature of the human body, typically via a catheter, either to block the flow of blood through a vessel making up that portion of the vasculature through the formation of an embolus or to form such an embolus within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration which may be dimensioned to engage the walls of the vessels. One anatomically shaped vasoocclusive device that forms itself into a shape of an anatomical cavity such as an aneurysm and is made of a pre-formed strand of flexible material that can be a nickel-titanium alloy is known from U.S. Pat. No. 5,645,558, which is specifically incorporated by reference herein. That vasooclusive device comprises one or more vasooclusive members wound to form a generally spherical or ovoid shape in a relaxed state. The vasooclusive members can be a helically wound coil or a co-woven braid formed of a biocompatible material, and the device is sized and shaped to fit within a vascular cavity or vesicle, such as for treatment of an aneurysm or fistula. The vasooclusive member can be first helically wound or braided in a generally linear fashion, and is then wound around an appropriately shaped mandrel or form, and heat treated to retain the shape after removal from the heating form. Radiopacity can be provided in the vasooclusive members by weaving in synthetic or natural fibers filled with powdered radiopaque material, such as powdered tantalum, powdered tungsten, powdered bismuth oxide or powdered barium sulfate, which can potentially be released during vascular surgery.

The delivery of such vasooclusive devices can be accomplished by a variety of means, including via a catheter in which the device is pushed through the catheter by a pusher to deploy the device. The vasooclusive devices, which can have a primary shape of a coil of wire that is then formed into a more complex secondary shape, can be produced in such a way that they will pass through the lumen of a catheter in a linear shape and take on a complex shape as originally formed after being deployed into the area of interest, such as an aneurysm. A variety of detachment mechanisms to release the device from a pusher have been developed and are known in the art.

For treatment of areas of the small diameter vasculature such as a small artery or vein in the brain, for example, and for treatment of aneurysms and the like, micro-coils formed of very small diameter wire are used in order to restrict, reinforce, or to occlude such small diameter areas of the vasculature. A variety of materials have been suggested for use in such micro-coils, including nickel-titanium alloys, copper, stainless steel, platinum, tungsten, various plastics or the like, each of which offers certain benefits in various applications. Nickel-titanium alloys are particularly advantageous for the fabrication of such micro coils, in that they can have super-elastic or shape memory properties, and thus can be manufactured to easily fit into a linear portion of a catheter, but attain their originally formed, more complex shape when deployed. Although various materials are more or less kink resistant when nickel-titanium alloys are dimensioned into wire smaller than approximately 0.010 inches in diameter, they can have low yield strength and can kink more easily, thus severely limiting the applications for such finely drawn wire in the fabrication of vasooclusive devices. As a further limitation to such applications, nickel-titanium alloys are also not radiopaque in small diameters, and a single nickel-titanium wire would need to be approximately 0.012 inches in diameter to be even slightly radiopaque. However, such a thickness of a single nickel-titanium wire would unfortunately also be relatively stiff and possibly traumatic to the placement site, particularly if used for treatment of delicate and already damaged areas of the small diameter vasculature such as an aneurysm in an artery or vein in the brain, for example.

One conventional guidewire for use in a catheter is known that is made of a high elasticity nickel-titanium alloy, and is useful for accessing peripheral or soft tissue targets. The distal tip of the guidewire is provided with a radiopaque flexible coil tip, and a radiopaque end cap is attached to the guidewire by a radiopaque ribbon. Such a construction is complex to manufacture, fragile and can potentially break off during use with undesirable results. A stretch resistant vasoocclusive coil is also known that can be made of a primary helically wound coil of platinum wire, with a stretch-resisting wire attached within the primary coil between two end caps. Unfortunately, such a construction is relatively difficult to fabricate and also fragile, allowing for the possibility of the fracture of the central radiopaque wire, the coil, the welds or some combination of them, and it can also potentially break off during use. Also, such a construction has a complex and nonlinear bending characteristic, dependent on the spacing of the coils and central wire and the radius of the bend of the coil.

From the above, it can be seen that vasoocclusive devices and their attendant deployment systems provide important improvements in the treatment of damaged neurovascular areas. However, there remain important limitations in the technology presently available to fabricate these devices. It would therefore be desirable to provide a structural element that can be incorporated into a stent, guidewire, micro-coil or the like, which offers the advantages of a shape memory alloy such as a nickel-titanium alloy, and that incorporates radiopaque material in a stable configuration that is not subject to breaking during use of the device, so that the device can be visualized under fluoroscopy. It would also be desirable to be able to create a variety of three dimensional vasoocclusive shapes that can be deployed from a catheter into an aneurysm or other defect and to thereby provide an efficient therapy for treatment of the defect. The present invention meets these and other needs.

SUMMARY OF THE INVENTION

Significant advances have been made in the treatment of neurovascular defects without resolution to surgery. More specifically, micro catheters have been developed which allow the placement of vasoocclusive devices in an area of the vasculature which has been damaged. In presently used techniques, the vasoocclusive devices take the form of spiral wound wires that can take more complex three dimensional shapes as they are inserted into the area to be treated. By using materials that are highly flexible, or even super-elastic and relatively small in diameter, the wires can be installed in a micro-catheter in a relatively linear configuration and assume a more complex shape as it is forced from the distal end of the catheter.

In order to gain the advantages presently being realized with micro-catheter therapies and procedures to repair damage to the vasculature in the brain and other vessels, shape memory materials such as nickel-titanium alloys have been incorporated in vasoocclusive devices to be placed by the catheters. However, the range of diameters of wire and the configurations of the resulting geometry of both the coils and the devices developed which can be used have been limited by both the relatively small diameter of wire that must be used to avoid trauma and allow housing within the catheter prior to deployment, and the requirement for larger diameters to provide for radiopaque markers and mechanical robustness. In many cases this has resulted in primary wire characteristics in the coil that are unacceptably stiff, very delicate, or subject to kinking. The present invention obtains significant advantages over such prior art devices by providing a cable of multiple strands of an alloy adapted to be used in catheters, stents, vasoocclusive devices, guidewires and the like, thus providing a kink resistant, high strength material with highly desirable performance characteristics which can be altered by construction details to suit a variety of interventional therapeutic procedures.

More specifically, it has been found that single strands of small diameter nickel-titanium alloys, as well as other metal alloys, used to form vasoocclusive devices can be kinked if twisted and pulled as can occur during or after deployment from a catheter, especially if the doctor wishes to withdraw a partially deployed coil because it is somehow incorrect in size, shape or length to repair the damage to the vessel. Also, single wire coils are more likely to cause trauma to the area to be treated if the wire is of a sufficient diameter to provide adequate tensile strength. Furthermore, such small diameter wires of some of these materials such as nickel-titanium, stainless steel and the like, are not generally radiopaque with currently available equipment, necessitating the use of radiopaque markers attached to the device, with the resultant possible diminution of functionality and increased diameter.

The present invention solves these and other problems by providing, in its broadest aspect, a micro-cable which includes at least one radiopaque strand to offer a continuous indication under fluoroscopy of the deployed configuration of the device incorporating the micro-cable. When combined with the benefits of a material such as nickel-titanium in the other strands of the micro-cable, numerous advantages are available from the use of this basic construction in interventional medicine.

Briefly, and in general terms, a presently preferred embodiment of the present invention provides for a multi-stranded micro-cable made of a suitable material such as stainless steel or a nickel-titanium alloy, with the cable including at least one radiopaque strand, made of platinum, tungsten or gold, in order to serve as a marker during a procedure. The multi-stranded micro-cable can be configured into a stent, guidewire, micro-coil or the like used in micro-catheters, for example, to restrict, reinforce, or to occlude areas of the small diameter vasculature such as an artery or vein in the brain, for example, for treatment of aneurysms and the like.

In one presently preferred embodiment, the invention accordingly provides for a multi-stranded micro-cable formed of a plurality of flexible strands of a super elastic material, and at least one radiopaque strand. In one presently preferred embodiment, the multi-stranded micro-cable comprises a plurality of flexible strands of nickel-titanium alloy, the micro-cable having at least one central axially disposed radiopaque wire, such as platinum, tungsten or gold, for example, in order to provide a radiopaque marker during vascular procedures. In this preferred embodiment, the construction of the invention places the lowest tensile strength and highest flexibility member, the radiopaque marker strand, in a position in the cable which results in minimum stress on that member; at the same time, the super elastic material is in the outer strands, which have the dominant affect on performance parameters, thus enhancing the benefits of the material. Another benefit associated with the invention compared to prior art devices is that the multiple stranded cable configuration, in addition to providing a highly flexible and resilient structure, eliminates the necessity of a safety wire, since the failure of a single strand will not cause a severing of the cable. Also, the construction prevents stretching of the cable in the event of failure of a single strand, which is a significant benefit compared to constructions which have a coil around a central safety wire.

In a second presently preferred embodiment, the invention includes a multi stranded cable constructed of multiple twisted strands of a suitable material such as a shape memory alloy or super elastic alloy of nickel-titanium, with one or more of the twisted strands consisting of a radiopaque material. The radiopaque strand may be one or more of the peripheral twisted strands and may also include one or more central strands of the cable. In a preferred aspect of the embodiment, the cable consists of six peripheral twisted strands and a central linear core strand, one or more of which can be of radiopaque material.

In a third aspect of the invention, the cable can be of linear strands that are arranged in a bundle and fastened or bound at intervals, or continuously, in order to maintain contact among the strands as the cable is bent. One or more of the strands may be radiopaque. This construction is adaptable to guidewires and other structures that must be pushable and/or torqueable, but still remain highly flexible and include radiopacity. Variations on this embodiment can include an outer sheath which consists of a solid or helically wound cover to provide enhanced torqueability and pushability. More specifically, the outer sheath can vary in thickness, stiffness of material or spring of the sheath members to provide desired variations in bending or stiffness of the cable. Such a construction is particularly adaptable to guidewires and the like, and can be varied in terms of the binding or outer layer to alter the torqueability of the cable, and the flexibility of the cable can be varied along its length by the number and sizes of the stranded members in the cable.

In a fourth aspect of the invention, one or more of the strands can be of a therapeutic material used to enhance treatment of the site after placement of the device. In one presently preferred embodiment of the invention, the cable includes twisted strands of wire around the periphery of the cable, at least one of which is radiopaque. The core of the cable contains a therapeutic agent such as human growth hormone, genetic material, antigens or the like that are intended to become active after placement. Such a construction can be adapted to a variety of interventional therapeutic treatments. In one aspect of this embodiment, one of the strands can have multiple functions, such as providing both a therapeutic effect and also contributing to the structural integrity of the cable. By using copper in such a micro-cable, for instance, the copper can enhance the use of a device made from the cable as on inter-uterine device, with the copper also contributing to the radiopacity and structural integrity of the micro-cable. In the event that such an effect is desired, the therapeutic strand can be placed on the exterior of the cable to enhance contact with the site to be treated.

In a fifth aspect of the invention, a three dimensional occlusive device is provided that is adapted to be inserted into a portion of a vasculature for occluding the portion of the vasculature for use in interventional therapy and vascular surgery, that comprises at least one multi-stranded micro-cable having a plurality of flexible strands of a resilient material, with at least one radiopaque strand to provide a radiopaque marker of the deployed configuration of a device made of the cable during vascular surgery. The occlusive device is configured to have a primary, collapsed coil configuration or shape, and an expanded, or secondary three dimensional coil configuration or shape, that can be generally helical, conical, or spherical shapes. The flexible strands in a multi-stranded micro-cable of the occlusive device can be helically wound, or can be configured as parallel, longitudinal strands. In a currently preferred embodiment, at least one of the strands comprises a super-elastic material. In another currently preferred embodiment, a plurality of the strands comprises a super-elastic material. One presently preferred super-elastic material comprises a nickel titanium alloy, that can be heat treated such that the alloy is highly flexible at a temperature appropriate for introduction into the body via a catheter, and after placement, the device will seek its minimum energy shape as originally formed and thereby take on a shape designed to optimize the therapeutic purposes desired for the device.

In another aspect of the invention, at least one of the strands comprises a shape memory material. In another currently preferred embodiment, a plurality of the strands are comprised of a shape memory material. One presently preferred shape memory material comprises a shape memory polymer. In one configuration, the strands of the micro-cable are arranged as exterior strands surrounding at least one interior strand, or core, and at least one radiopaque strand is disposed in the micro-cable, either centrally, axially disposed in the bundle of strands, or in the exterior strands surrounding the central core. The micro-cable can include a plurality of radiopaque strands, such as platinum, gold, or tungsten.

In the fifth aspect of the invention, at least one of the strands in the core or exterior strands can comprise a therapeutic agent, such as a copper or copper alloy wire or any of a variety of therapeutically active metals, alloys or components, a fiber such as Dacron (polyester), polyglycolic acid, polylactic acid, fluoropolymers, nylon, polyaramid fiber (e.g.Kevlar®), or silk chosen for thrombogenicity. Since the micro-cable consists of stranded parts, one or more strands may be longer than others, or even intermittently terminated, to thereby extend beyond the diameter of the remaining strands and thereby increase the therapeutic effect of that strand. Alternatively, at least one of the strands can be coated with or impregnated with a therapeutic material, which can include, but is not limited to, any one or combination of human growth hormone, genetic material, antigens, hydrogels, collagen, bio-absorbable polymers such as lactic acids/glycolic acids, caprolactam or microcellular foam. In addition, the therapeutic element can comprise a means to conduct energy, such as an optical fiber to conduct light energy.

In the fifth aspect of the invention, the strands of the micro-cable can also be bundled by at least one outer cover or sheath to constrain the strands of the micro-cable about a longitudinal axis to produce a composite banded cable. The outer sheath can comprise a containment strand wound about the strands and made of a low friction material, such as a fluoropolymer, for example, or a heat shrinkable plastic tube. In one feature of the fifth aspect of the invention, a plurality of heat shrinkable plastic covers are placed over the strands of the micro-cable to provide bending stiffness in the cable. The strands of the micro-cable can be banded at intervals by a plurality of bands. In another variation, a plurality of micro-cables that are arranged as parallel, longitudinal micro-cables or a helically wound micro-cables to form a composite cable can have an exterior wrapped cover that can be wound at greater or lesser intervals along the outside to provide variations in the torqueability and stiffness of the composite cable. Also, the thickness and width of the wrapping cover, as well as its material composition along the composite cable can vary in cross section along the length of the composite cable to provide bending stiffness to said cable which varies with the position on said cable. Also, the number to strands and the degree to which they extend along the composite cable can be varied within the sheath, and the outer sheath itself can be multi-layered with different materials in order to provide a graduated bending and stiffness characteristic over the length of the cable. The occlusive device thus can be formed of a plurality of micro-cables in order to provide desired bending and strength characteristics, either as helically wound microcables, or parallel longitudinal micro-cables having a collapsed composite cable configuration and an expanded composite cable configuration with a secondary shape. In another feature of the fifth aspect of the invention, the composite cable can further comprise at least one longitudinal sensing element for sensing a parameter, such as an optical imaging element, i.e., where the sensing element can comprises an optical fiber. Alternatively, the sensing element can comprise a thermal imaging element, or an ultrasound imaging element, for example.

In a further aspect of the invention, the form about which the three dimensional shape is wound is formed from metal, ceramic or other heat resistant material and has formed within it the path desired for the micro-cable corresponding to the shape. For example, the form can be of a spherical configuration, with the surface containing channels into which the cable is laid prior to heat treating. The channels can be arranged so that the resultant shape is kink resistant and relatively easy to withdraw without kinking. The form can also contain passages through which the cable can pass to advantageously form the shape.

After the cable is wound around the form, the form and cable can be heat treated to cause the cable material to adopt the shape of the form as a low energy shape. The cable can then be removed from the form and put into a catheter-introducer prior to use in intravascular therapy.

These and other aspects and advantages of the invention will become apparent from the following detailed description and the accompanying drawings, which illustrate by way of example the features of the invention.

BRIEF DESCRIPTION OF THE DRAWINGS

FIG. 1 is a perspective of a radiopaque microstrand cable constructed according to the invention.

FIG. 2 is a cross-section at 2—2 of FIG. 1.

FIG. 8 is an illustration of a spherical vasooclusive coil formed with cable of the invention deployed within an aneurysm.

FIG. 9 is an alternate preferred embodiment of the invention including a plurality of radiopaque strands within the cable.

FIG. 10 is an alternate preferred embodiment incorporating a therapeutic member within the radiopaque cable of the invention.

FIG. 13 is an alternative embodiment to the embodiment of FIG. 12 wherein the external binding of the cable represents a sheath wound about the cable.

FIGS. 14a and 14b are perspectives of alternative embodiments of the embodiment of FIG. 13.

FIG. 15 is a cross-section of an alternative embodiment in which a plurality of multi-strand cables are included within an external sheath surrounding the cable.

FIG. 16 is a perspective view of the embodiment of FIG. 14.

DETAILED DESCRIPTION OF THE PREFERRED EMBODIMENTS

Figure 3:
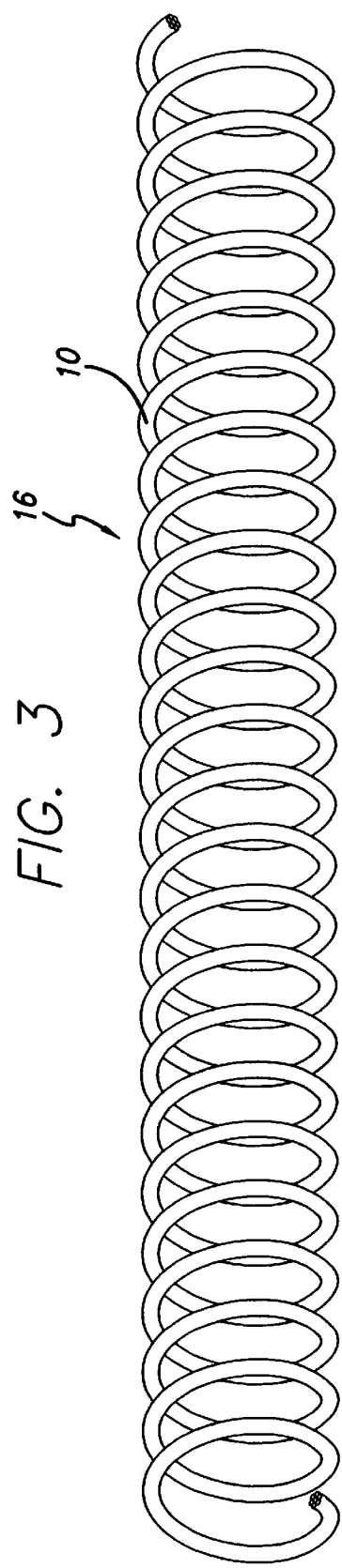
FIG. 3 is a helical vasooclusive coil formed of the cable of the invention.

While nickel-titanium alloys are useful in forming super-elastic or shape memory interventional devices, micro-coils formed of very small diameter wires of nickel-titanium alloy material for treatment of areas of the small diameter vasculature such as an artery or vein in the brain, for treatment of aneurysms and the like, for example, can have relatively low yield strengths and are somewhat subject to kinking, even if made of super-elastic alloy. This can create problems if the coil is to be withdrawn after being emplaced by the doctor, as for instance, if the device is too small to effectively fill the cavity to be treated. Furthermore, even solid wires of a size suitable for use in interventional devices are not very radiopaque.

As is illustrated in the drawings, which are provided for the purposes of illustration and not by way of limitation, the invention is embodied in a multi-stranded micro-cable formed of a plurality of flexible strands of a resilient material with the cable including at least one radiopaque strand. In a presently preferred embodiment of the invention illustrated in FIG. 1, the multi-stranded micro-cable 10 is approximately 0.0015 to 0.009 inches in diameter, and comprises a plurality of flexible strands 12 of nickel-titanium alloy, with at least one centrally, axially disposed radiopaque wire 14 which is approximately from 0.0005 to 0.003 inches in diameter. While the above stated diameters represent those presently known to be compatible with the invention, larger or smaller diameters may be useful for particular applications. The central radiopaque wire 14 can be formed of platinum or gold, for example, or other similar suitable radiopaque metals, in order to provide a radiopaque marker for the deployed configuration of a device made of the cable during vascular surgery.

There are numerous benefits to the novel construction of the invention for use in interventional devices and the like. By using the stranded or micro-cable construction of the invention, a device made from the micro-cable becomes virtually kink resistant compared to the single strand wires now commonly used in micro-coils. The multi-strand cable construction of the invention allows the micro-wires of the cable to slip across each other and reinforce each other rather than break or take a set. Also, by incorporating a stranded radiopaque material such as platinum, tungsten or gold into the cable construction, the device is radiopaque in sizes much smaller than with other constructions. The micro-cable construction of the invention can be used to produce soft, kink resistant, radiopaque stents, guidewires, guidewire distal tips, and micro-coils.

FIG. 2 is a cross-section of the micro-cable of FIG. 1 at 2—2 illustrating one presently preferred arrangement of the strands within the cable. In this embodiment, the exterior strands 12 are formed of a resilient material chosen to provide the characteristics desired for a specific application in interventional therapies. In a presently preferred embodiment, this material is a nickel titanium super-elastic alloy which is heat treated such that the alloy is highly flexible at a temperature appropriate for introduction into the body via a catheter. By choosing such a material for microcoils and the like, the devices formed from the micro-cable can be relatively easily placed into the appropriate body cavity and after placement, the device will take on a shape designed to optimize the therapeutic purposes desired for the device. As illustrated in FIG. 2, such a cable can have a central core 14 of a radiopaque material such as gold or platinum, thus dramatically enhancing the radiopacity of the cable. Even a solid super-elastic wire of the same diameter as the cable would have substantially less radiopacity than the cable of the invention with the central gold or platinum wire and the construction of the invention provides numerous other highly desirable characteristics. Among these characteristics is the relative flexibility and resistance to kinking of the cable compared to an equivalent single wire and substantially greater accommodation of the cable to bending, etc., with resultant lessening of trauma to the surrounding tissue and ease of placement in a small body cavity.

Figure 5:
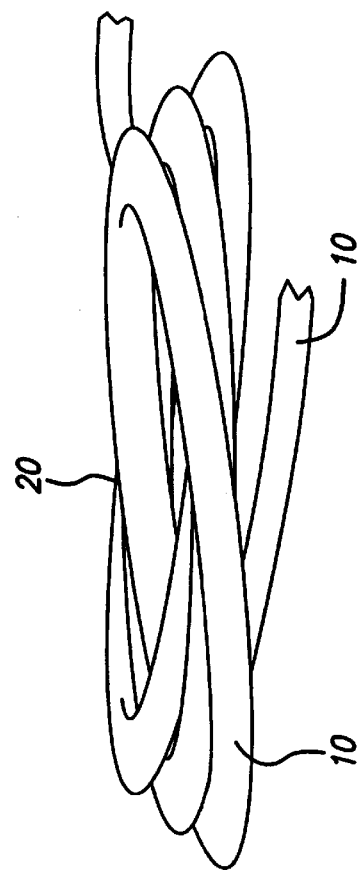
FIG. 5 is a stacked coil vasooclusive device formed using the cable of the invention.
Figure 4:
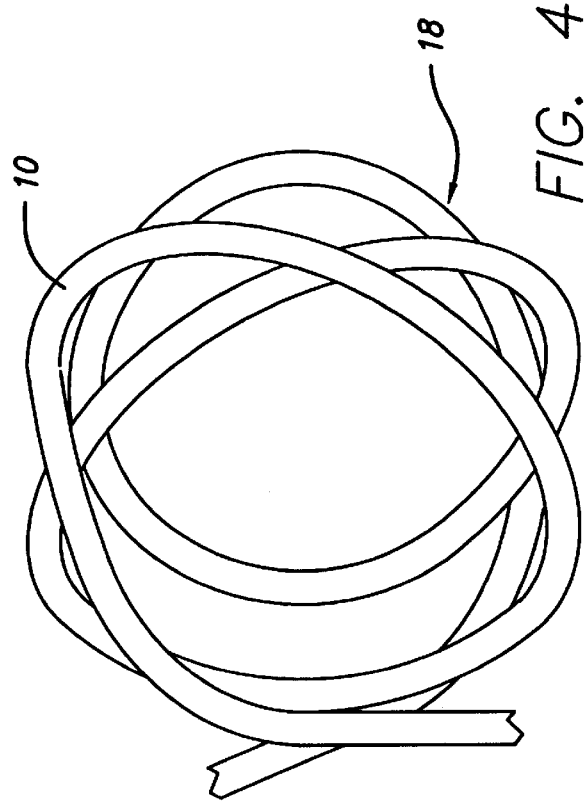
FIG. 4 is a spherical vasooclusive structure formed using the cable of the invention.

One advantageous application of the invention is to vasoocclusive devices formed of the micro-cable for insertion into aneurysms and other vascular defects for the purpose of occluding flow to the aneurysm. FIG. 3 illustrates a helically wound coil 16 of micro-cable 10 which is formed to fit within a micro-catheter for insertion into an area upon which a therapeutic procedure is to be performed. While a helical coil is illustrated, it will be appreciated that numerous other secondary shapes can be formed from the cable of the invention, as will be described further below. More specifically, as illustrated in FIG. 4, a three dimensional, essentially spherical, device 18 can be formed of the cable 10, (or even of a coil of the cable, if appropriate) at a temperature sufficient to heat treat the material and thereby create a memory of the desired shape. The device is then inserted into a catheter from which it may be deployed into an aneurysm or the like. The teachings of U.S. Pat. No. 5,645,558 describe the construction of such a device out of flexible wire and are incorporated by referenced herein. FIG. 5 illustrates a collapsed coil configuration 20 for a vasoocclusive device which also can be formed from the cable of the invention and is used for the purposes of insertion into aneurysms and other defects that have relatively large entry necks compared to their internal volume.

Figure 6:
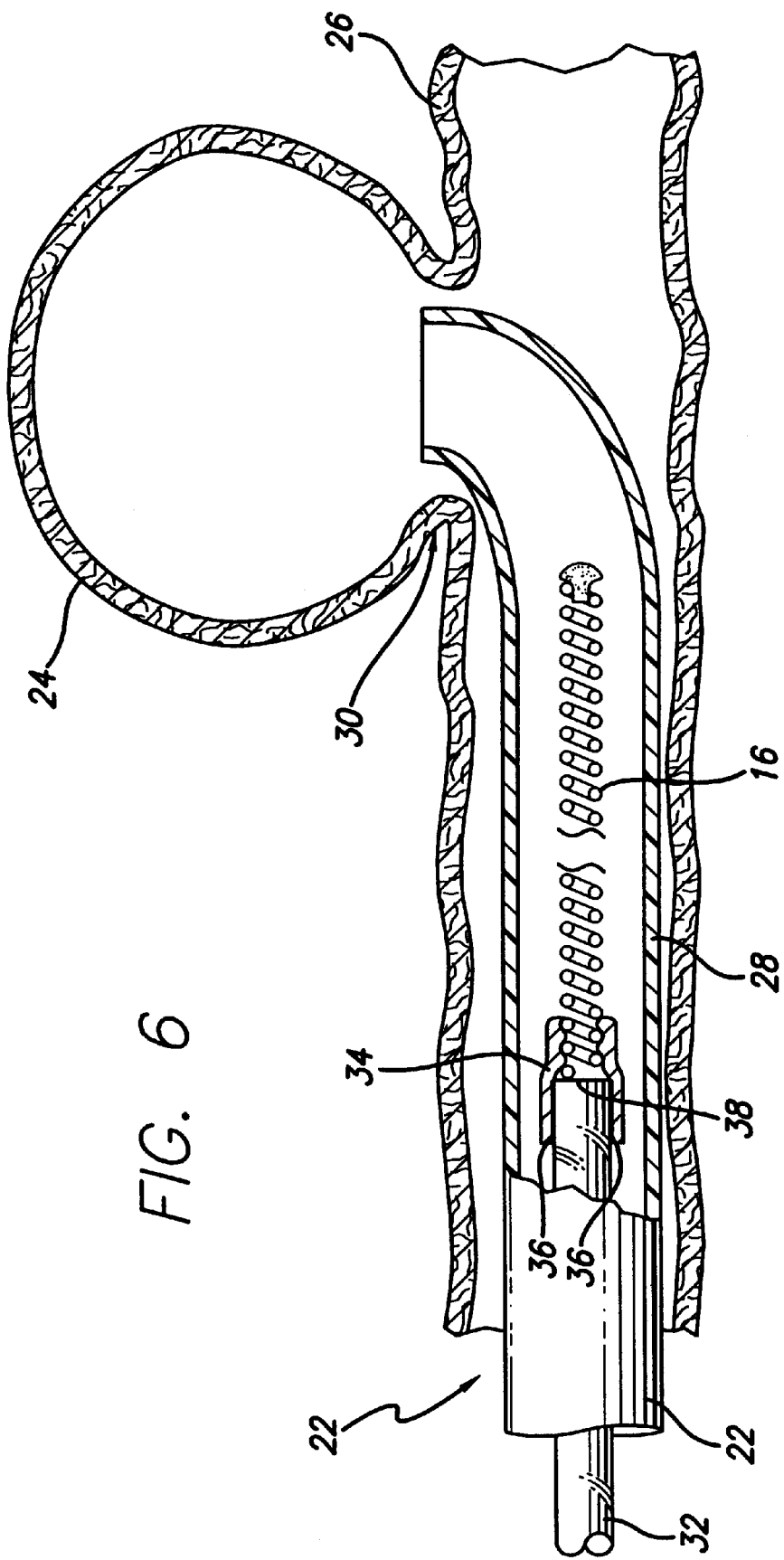
FIG. 6 is a cross section of a vascular member with an aneurysm illustrating the approach of a vasooclusive coil towards the aneurysm.
Figure 7:
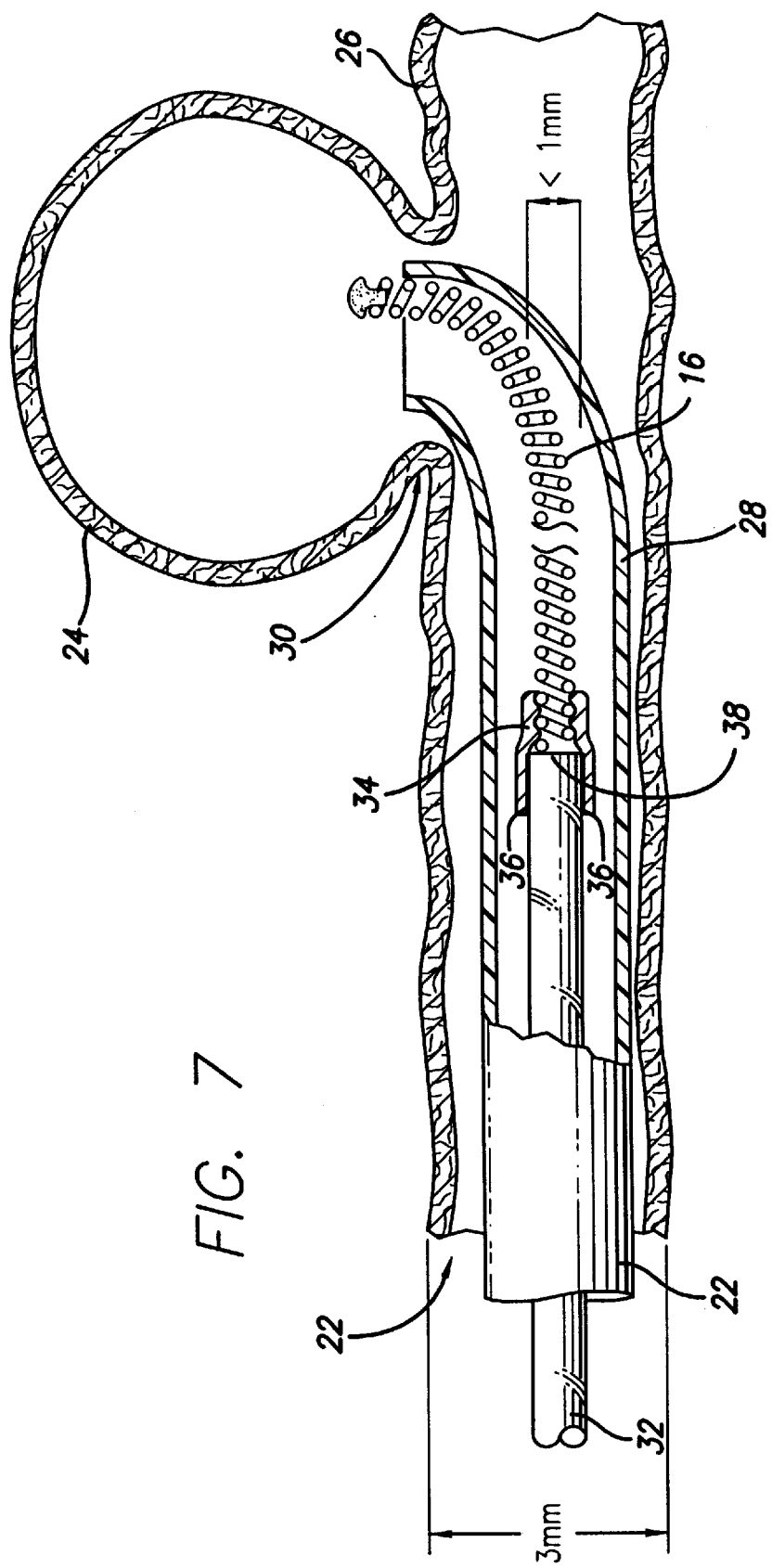
FIG. 7 is an illustration of a vasooclusive coil which has been introduced into an aneurysm preparatory to being deployed within the aneurysm.

FIG. 6 is an illustration of a catheter 22 using a coil 16 as a vasoocclusive device made of the present invention and used for insertion into an aneurysm 24 projecting laterally from a blood vessel 26. The coil 16 is contained within the outer housing 28 of a micro-catheter that is used to house the coil prior to deployment. The end of the catheter housing 28 is introduced into the opening 30 of the aneurism 24 by use of a guide wire (note shown). Thereafter, the vasoocclusive coil 16, and a pusher 32 are introduced into the catheter to provide for insertion of the vasoocclusive device into the aneurysm. In a presently preferred embodiment, the coil 16 formed of the cable of the invention is retained to an optical fiber pusher 32 which is attached to the coil by a collar of shape memory plastic material 34 as described in co-pending application Ser. No. 08/986,004 the disclosure of which are incorporated herein by reference. As shown in FIG. 7, the coil is introduced into the aneurysm and is then pushed from the micro-catheter until it fills the cavity.

Those skilled in the art will recognize that it is sometimes the case that the vasooclusive device must be withdrawn after it is fully or partly inserted into the aneurysm. In such a case, there is a danger that the coil will be stretched beyond its elastic range or kink, or otherwise deform and make withdrawal difficult. Those skilled in the art will also recognize that it is sometimes advantageous to form vasoocclusive devices of secondary shapes which are based upon a basic configuration of a coil or the like. The present invention includes such applications within the scope of the invention. However, when vasooclusive devices made of even super-elastic material are used, it is sometimes the case that the devices will be stretched or kinked when withdrawal is attempted. The cable of the present invention substantially reduces the probability that kinking or stretching beyond yield will occur in a given instance, while at the same time providing radiopacity not available with other constructions. Thus, the present invention represents an important forward step in the technology of interventional therapy.

In one presently preferred embodiment, the shape memory collar 34 is heated to a temperature which allows it to be shrunk onto coil 16. The collar is attached to optical fiber pusher 32 by an adhesive 36 which retains high strength at temperatures beyond the shape memory material transition point. After insertion, and when the operator is satisfied that the device is properly deployed, light energy from a source of coherent light is introduced into the proximal end of the optical fiber (not shown) and propagated in the distal end 38 of the fiber to cause the shape memory material collar 34 to return to its previous shape and release coil 16. Those skilled in the art will recognize that the invention can also be used with a variety of other placement catheter systems, and it is not intended that the invention be limited to the placement concepts illustrated by way of example.

Those skilled in the art will recognize that a number of shaped devices may be introduced into an area to be treated depending upon its geometry and the number of devices to be inserted. FIG. 8 illustrates an essentially spherical device 18 which has been deployed into such an aneurysm but it will commonly be found that a device such as that shown would then be supplemented by a further coiled device inserted within the space inside the spherical device to completely occlude flow from the artery to the aneurysm.

While one presently preferred implementation of the micro-cable of the invention has been illustrated, those skilled in the art will appreciate that other variations of the invention may have advantages for certain purposes. FIG. 9 is an example of one such construction 40 in which radiopacity is more desirable than in other forms and for that reason a number of radiopaque strands 42, in this illustration four in number, are formed into the cable along with three resilient material strands 44. It will also be appreciated that a larger or smaller number of strands may be incorporated into a given cable and the cables may be formed of multiple cables in order to provide desired bending and strength characteristics. It will also be appreciated by those skilled in the art that the invention is adaptable to the use of a variety of materials which by themselves would not have been easily adaptable to micro devices for interventional therapies. For instance, materials such as copper are useful for intrauterine devices and the like, but copper wire, even when heavily alloyed, has certain limitations for use in such devices. By use of the present invention, composite cables incorporating one or more strands of a desired material can be configured with other strands providing strength, flexibility, shape memory, super-elasticity, radiopacity or the like for previously unavailable characteristics in micro devices.

The invention is also adaptable to numerous other purposes. FIG. 10 illustrates a cross-section of a further preferred embodiment in which radiopaque strands 42 and resilient strands 44 form a portion of the cable 46 and a therapeutic agent 48 is contained in one of the strands. Such a therapeutic agent can include human growth hormone, hydrogels, or a variety of other agents which will serve to provide desired therapeutic capabilities when placed within a specific area of the body being treated by use of the micro-catheter. Depending upon the application of the therapeutic agent, its method of action and the delay, if any, in the time after placement in which the therapeutic action is desired, the agent strand may be placed in any of a variety of positions with the cable, from core wire outward. Also, it may be desirable to coat one or more strands with a therapeutic material for certain purposes. At least one of the strands in the core or exterior strands can comprise a therapeutic agent, such as a copper or copper alloy wire or any of a variety of therapeutically active metals, alloys or components, a fiber such as Dacron (polyester), polyglycolic acid, polylactic acid, fluoropolymers, nylon, polyaramid fiber (e.g.Kevlar®), or silk chosen for thrombogenicity. Since the micro-cable consists of stranded parts, one or more strands may be longer than others, or even intermittently terminated, to thereby extend beyond the diameter of the remaining strands and thereby increase the therapeutic effect of that strand. Alternatively, at least one of the strands can be coated with or impregnated with a therapeutic material, which can include, but is not limited to, any one or combination of human growth hormone, genetic material, antigens, hydrogels, collagen, bio-absorbable polymers such as lactic acids/glycolic acids, caprolactam or microcellular foam. In addition, the therapeutic element can comprise a means to conduct energy, such as an optical fiber to conduct light energy, or a means to conduct electrical energy, such as a means to conduct radio frequency energy. Such constructions are contemplated within the scope of the invention.

It is also contemplated within the scope of the invention that one or more of the strands of the micro-cable is longer than the others, and perhaps intermittently terminated, to thereby produce a micro-cable in which the therapeutic strands extend to a greater diameter than the other strands to thus increase the therapeutic effect of the therapeutic stand. Such a construction is particularly advantageous if increased thrombogenicity is desired, while maintaining structural continuity and radiopacity for the micro-cable.

Figure 12:
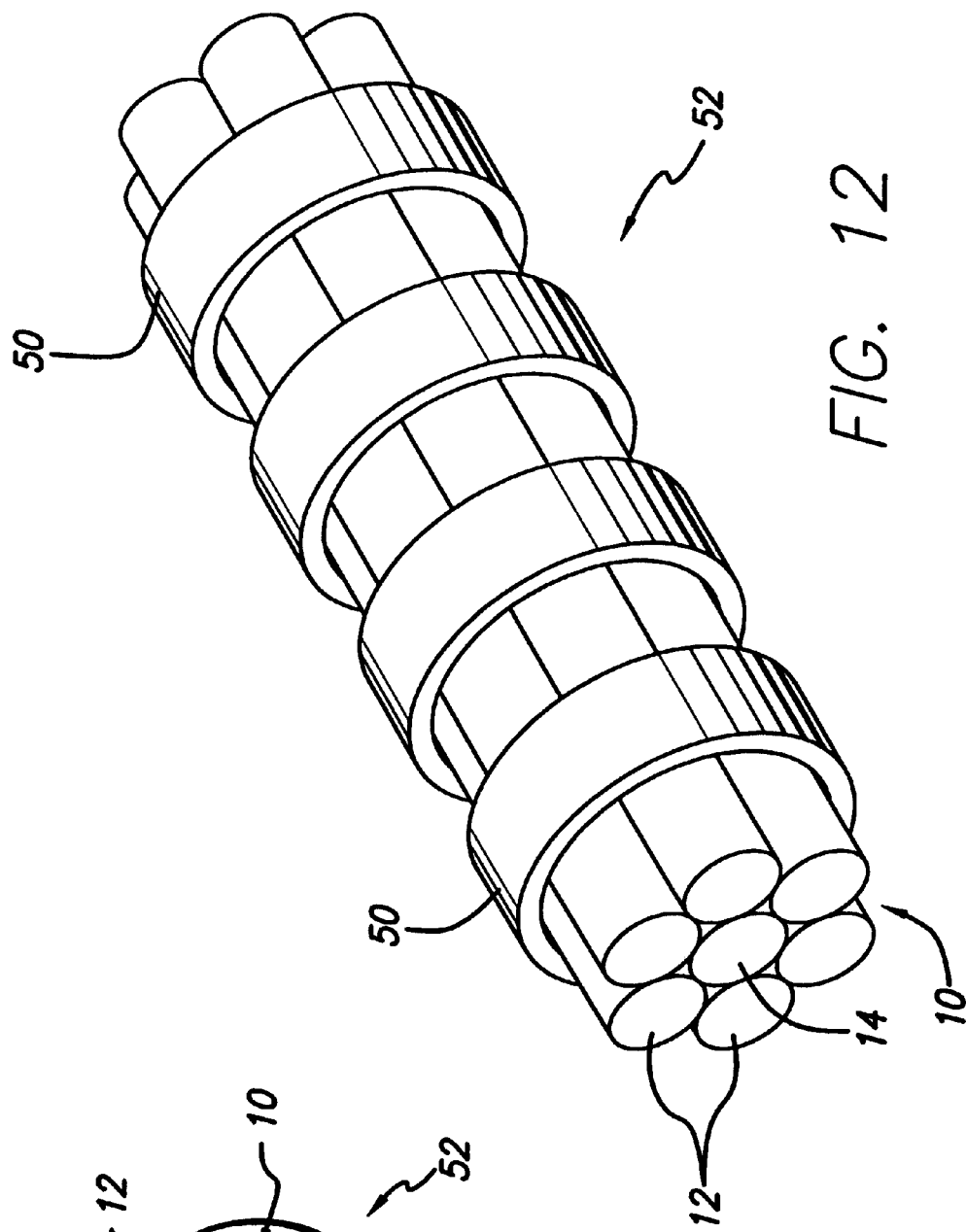
FIG. 12 is a perspective view of the embodiment of FIG. 11.
Figure 11:
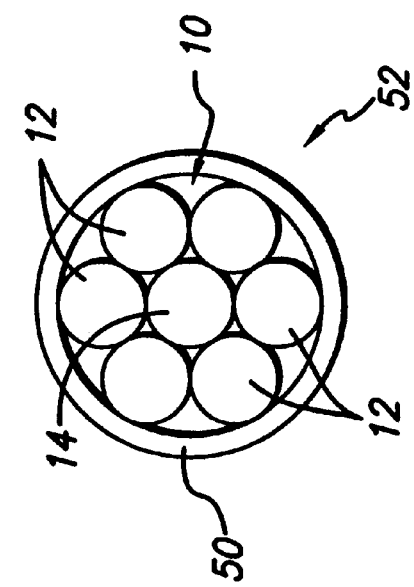
FIG. 11 is an alternate preferred embodiment of the present invention wherein strands of the cable are arranged within an exterior binding consisting of multiple straps about the cable.

FIG. 11 illustrates a cross-section of an additional presently preferred embodiment of the invention in which the strands 12, 14 of the micro-cable 10 are bundled and banded at intervals by bands 50 to produce a composite banded cable 52 in order to provide increased flexibility without unraveling or dislocation of the strands in the cable. FIG. 12 is a perspective view of the banded cable 52 of this embodiment. While the illustrated configuration shows the strands being laid parallel within the cable, it is also possible in this construction to include both twisted cables as the primary cables 10 within the outer bands 50 to form the composite cable 52. This configuration can use one or more longitudinal strands 14 which are radiopaque, thus providing a continuous indication of radiopacity within the cable. The composite cable can further comprise at least one longitudinal sensing element for sensing a parameter, such as an optical imaging element, i.e., where the sensing element can comprises an optical fiber. Alternatively, the sensing element can comprise a thermal imaging element, or an ultrasound imaging element, for example. As a further alternative embodiment, it is possible for the longitudinal cable 52 to be formed of a single inner cable 10 with bands 50.

FIG. 13 illustrates a further embodiment of the invention in which longitudinal strands of cables 54 are contained within a wound cover 56 for the purposes of providing a composite guide wire or the like 58 having improved torqueability. The strands of the micro-cable can also be bundled by at least one outer cover or sheath to constrain the strands of the micro-cable about a longitudinal axis to produce a composite banded cable. The outer sheath can comprise a containment strand wound about the strands and made of a low friction material, such as a fluoropolymer, for example, or a heat shrinkable plastic tube. In one feature of the fifth aspect of the invention, a plurality of heat shrink plastic covers are placed over the strands of the micro-cable to provide bending stiffness in the cable. Such a construction has particular advantages for guidewire designs having improved radiopacity in very small diameters. It will be appreciated that in this configuration, as well as the other longitudinally arranged multi-stranded cables, the number of strands and the degree to which they extend along the cable within the sheath is a variable which can be used to provide increased stiffness, pushability and torqueability in some sections with greater flexibility in others. Additionally, composite cables according to the invention can incorporate additional elements normally not available in solid guide wires, such as optical, thermal or ultrasound imaging elements, therapeutic agent delivery catheters, and can take advantage of materials which are not readily adaptable to prior art catheter or guide wire designs incorporating a primary wire structured element. FIGS. 14a and 14b illustrate a further variable available because of the invention; the exterior wrapped cover 56 can be wound at greater or lesser intervals 60 along the outside to provide variations in the torqueability and stiffness of the composite cable. Also, the thickness and width of the wrapping cover 56, as well as its material composition along the composite guide wire 58, can offer further capabilities for customizing the design for various applications. These advantages can be combined with the benefits of shape memory or super-elastic alloys to create guidewires and other devices with heretofore unavailable capabilities.

FIG. 15 illustrates a cross-section of a micro-cable according to the invention which has at least one overall exterior sheath to contain the micro-cable. The micro-cable may be made of one or more multiple strand elements which may further include twisted or longitudinal strands within their construction. The sheath may also be used to control the torqueability characteristics of the cable and as discussed in co-pending application, Ser. No. 08/986,004, the sheath may be multi-layered with different materials in order to provide a graduated bending and stiffness characteristic over the length of the cable.

It will be appreciated that a three dimensional occlusive device adapted to be inserted into a portion of a vasculature for occluding the portion of the vasculature for use in interventional therapy and vascular surgery, can be formed as described above, from at least one multi-stranded micro-cable having a plurality of flexible strands of a resilient material, with at least one radiopaque strand to provide a radiopaque marker for the device during vascular surgery. The occlusive device is configured to have a primary coil shape, as illustrated in FIG. 5, and an expanded secondary three dimensional coil configuration or shape, that can be generally helical, conical, or spherical shapes, such as the spherical shapes illustrated in FIGS. 4 and 8. A mandrel suitable for making such three dimensionally shaped occlusive devices can be formed of a refractory material, such as alumina or zirconia, for example. The mandrel typically has the general three dimensional shape that the occlusive device will be given, and can have a generally helical, conical, or spherical shape, or can have a unique shape designed to provide such a form to the occlusive device to fit a particular vascular structure to be treated. The mandrel forms a support for the winding and heat treatment of the micro-cable, plurality of microcables, or composite micro-cable occlusive device as described above, and ideally will not contaminate the occlusive device during heat treatment of the device. The surface of the mandrel preferably has a plurality of circumferential grooves for aligning the occlusive device as it is wound on the mandrel. The surface of the mandrel may also have one or more apertures for receiving one or more ends of the micro-cable, plurality of microcables, or composite micro-cable, to assist winding into the desired form.

The wound occlusive device is then heat treated at a suitable temperature and a sufficient period of time to impart the form to the shape memory material included in the device. While heat treatment at a temperature of about 1100° F. for approximately 4 hours or more is typically sufficient to impart the form to the occlusive device when the shape memory material is a nickel titanium super-elastic alloy, but when the occlusive device includes fibers or a therapeutic agent that can be affected by heat, the temperature utilized can be substantially lowered, and the duration of heat treatment adjusted accordingly, as will be appreciated by those skilled in the art. Alternatively, if the therapeutic agent is not amenable to elevated temperatures, it may be added after formation of the three dimensional shape. After the heat treatment, the occlusive device is removed from the mandrel, and cold worked into the desired collapsed primary configuration for placement into a catheter or cannula for use. It will be appreciated that those techniques can also be used for a variety of cables produced according to the invention, including those which use shape memory materials other than nickel-titanium alloys. When the occlusive device reaches its destination in the vasculature during vascular therapy, it assumes the secondary relaxed and expanded three dimensional shape imparted from the heat treatment on the mandrel.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A device for use in interventional therapy and vascular surgery, adapted to be inserted into a portion of a vasculature, comprising:
   at least one multi-stranded micro-cable having a collapsed primary coil configuration and an expanded secondary configuration with a three dimensional shape, each said multi-stranded micro-cable having a plurality of flexible strands of a shape memory material, and at least one radiopaque strand to provide a radiopaque marker of the deployed configuration of the device.

2. The device of claim 1, wherein said secondary three dimensional shape is generally spherical.

3. The device of claim 1, wherein said secondary three dimensional shape is generally helical.

4. The device of claim 1, wherein said secondary three dimensional shape is generally conical.

5. The device of claim 1, wherein said plurality of strands are helically wound.

6. The device of claim 1, wherein said plurality of flexible strands are parallel longitudinal strands.

7. The device of claim 1, wherein at least one of said plurality of strands comprises a super-elastic material.

8. The device of claim 1, wherein said plurality of strands are comprised of a super-elastic material.

9. The device of claim 8, wherein said super-elastic material comprises a nickel titanium alloy.

10. The device of claim 1, wherein said shape memory material comprises a nickel-titanium alloy.

11. The device of claim 10, wherein said shape memory nickel-titanium alloy is heat treated such that the alloy is highly flexible at a temperature appropriate for introduction into the body via a catheter, and after placement, the device will take on a shape designed to optimize the therapeutic purposes desired for the device.

12. The device of claim 1, wherein said shape memory material comprises a shape memory polymer.

13. The device of claim 1, wherein at least one of the strands comprises a therapeutic agent.

14. The device of claim 13, wherein said strand comprising a therapeutic agent is wound into said micro-cable so that at least a portion of said strand projects beyond the diameter of the other strands in said cable.

15. The device of claim 13, wherein said therapeutic agent comprises a metal wire selected from the group consisting of copper and copper alloys.

16. The device of claim 13, wherein said therapeutic agent comprises a fiber selected from the group consisting of polyester, polyglycolic acid, polylactic acid, fluoropolymers, nylons, polyaramid fiber and silk chosen for thrombogenicity.

17. The device of claim 13, wherein at least one of the strands is impregnated with said therapeutic agent.

18. The device of claim 13, wherein at least one of the strands is coated with said therapeutic agent.

19. The device of claim 13, wherein said therapeutic agent is selected from the group consisting of human growth hormone, genetic material, antigens and hydrogels.

20. The device of claim 13, wherein said therapeutic agent comprises at least one component selected from the group consisting of hydrogel, collagen, and bio-absorbable polymers including lactic acids, glycolic acids, caprolactam and microcellular foams.

21. The device of claim 15, wherein said therapeutic agent comprises means to conduct energy.

22. The device of claim 21, wherein said means to conduct energy comprises an optical fiber to conduct light energy.

23. The device of claim 21, wherein said therapeutic means comprises means to conduct electrical energy.

24. The device of claim 23, wherein said means to conduct electrical energy comprises means to conduct radio frequency energy.

25. The device of claim 13, wherein said therapeutic agent is disposed axially in a central core.

26. The device of claim 1, wherein said plurality of strands comprises a plurality of exterior strands surrounding at least one interior strand.

27. The device of claim 1, wherein said plurality of strands comprises a plurality of exterior strands surrounding a central core.

28. The device of claim 1, wherein said radiopaque strand comprises at least one centrally, axially disposed radiopaque wire.

29. The device of claim 1, wherein said radiopaque wire is made of platinum.

30. The device of claim 1, wherein said radiopaque wire is made of tungsten.

31. The device of claim 1, wherein said radiopaque wire is made of gold.

32. The device of claim 1, wherein said micro-cable comprises a plurality of radiopaque strands.

33. The device of claim 1, wherein said micro-cable comprises four radiopaque strands.

34. The device of claim 33, wherein said micro-cable comprises three shape memory material strands.

35. The device of claim 1, wherein said micro-cable includes a central core.

36. The device of claim 35, wherein said central core of said micro-cable comprises copper.

37. The device of claim 35, wherein said central core of said micro-cable comprises a copper alloy.

38. The device of claim 1, wherein said radiopaque wire is approximately 0.0005 to 0.0030 inches in diameter.

39. The device of claim 38, wherein said strands of the micro-cable are bundled by a plurality of bands disposed at intervals along said micro-cable to produce a composite banded cable.

40. The device of claim 39, wherein said composite cable comprises a single inner micro-cable.

41. The device of claim 38, further comprising at least one longitudinal element for sensing a parameter.

42. The device of claim 41, wherein said longitudinal element for sensing a parameter comprises an optical imaging element.

43. The device of claim 41, wherein said longitudinal element for sensing a parameter comprises an optical fiber.

44. The device of claim 41, wherein said longitudinal element for sensing a parameter comprises a thermal imaging element.

45. The device of claim 41, wherein said longitudinal element for sensing a parameter comprises an ultrasound imaging element.

46. The device of claim 1, wherein said strands of the micro-cable are bundled by at least one outer cover to produce a composite banded cable.

47. The device of claim 46, wherein said outer cover comprises a sheath to constrain said strands of said micro-cable about a longitudinal axis.

48. The device of claim 47, wherein said sheath comprises a containment strand wound about said longitudinal strands.

49. The device of claim 48, wherein said sheath is made of low friction material.

50. The device of claim 48, wherein said sheath is made of a fluoropolymer.

51. The device of claim 48, wherein said strands are laid parallel within the composite banded cable.

52. The device of claim 48, wherein said strands are twisted within the composite banded cable.

53. The device of claim 48, wherein the width of the outer cover is varied along the composite cable.

54. The device of claim 47, wherein said sheath comprises a heat shrinkable plastic tube.

55. The device of claim 47, wherein outer covering comprises a plurality of layers formed of different materials in order to provide a graduated bending and stiffness characteristic over the length of the cable.

56. The device of claim 46, wherein said outer cover comprises an outer sheath of material to provide bending stiffness and constrain said longitudinal strands about said longitudinal axis.

57. The device of claim 56, wherein said sheath comprises a plurality of heat shrink plastic covers placed to provide bending stiffness in said cable which varies with the position on said cable.

58. The device of claim 56, wherein said exterior wrapped cover is wound at varying intervals along the outside to provide variations in the torqueability and stiffness of the composite cable.

59. The device of claim 46, wherein said outer covering varies in cross section along its length to provide bending stiffness of said composite cable which varies along said composite cable.

60. The device of claim 46, wherein the number of strands and the degree to which they extend along said composite cable within the outer covering varies along said composite cable.

61. The device of claim 46, wherein said composite micro-cable comprises a plurality of micro-cables disposed within said outer cover in order to provide desired bending and strength characteristics.

62. The device of claim 61, wherein said plurality of micro-cables are helically wound within said outer cover.

63. The device of claim 61, wherein said plurality of micro-cables extend parallel and longitudinally within said outer cover.

64. The device of claim 61, wherein said composite cable has a collapsed primary configuration and an expanded secondary configuration with a secondary shape.

65. The device of claim 64, wherein said secondary shape is three dimensional.

66. The device of claim 64, wherein said secondary shape is spherical.

67. The device of claim 64, wherein said secondary shape is helical.

68. The device of claim 64, wherein said secondary shape is conical.

69. The device of claim 61, wherein said plurality of micro-cables are banded at intervals by a plurality of bands.

70. The device of claim 1, wherein said multi-stranded micro-cable is approximately 0.0021 to 0.0045 inches in diameter.

71. The device of claim 70, further comprising at least one longitudinal element for sensing a parameter.

72. The device of claim 1, further comprising at least one longitudinal element for sensing a parameter.

73. A composite device for use in interventional therapy and vascular surgery adapted to be inserted into a portion of a vasculature, comprising:

at least one multi-stranded micro-cable having a collapsed primary coil configuration and an expanded configuration with a secondary three dimensional shape, each said multi-stranded micro-cable having a plurality of flexible strands of a shape memory material, and at least one radiopaque strand to provide a radiopaque marker of the deployed configuration of a device made of the micro-cable; and at least one outer cover disposed over each said multi-stranded micro-cable to produce a composite banded cable.

74. The composite device of claim 73, wherein said secondary three dimensional shape is generally spherical.

75. The composite device of claim 73, wherein said secondary three dimensional shape is generally helical.

76. The composite device of claim 73, wherein said secondary three dimensional shape is generally conical.

77. The composite device of claim 73, wherein said plurality of strands are helically wound.

78. The composite device of claim 73, wherein said plurality of flexible strands are parallel longitudinal strands.

79. The composite device of claim 73, wherein at least one of said plurality of strands comprises a super-elastic material.

80. The composite device of claim 79, wherein said super-elastic material comprises a nickel titanium alloy.

81. The composite device of claim 73, wherein a plurality of said flexible strands are comprised of a super-elastic material.

82. The composite device of claim 73, wherein said shape memory material comprises a nickel-titanium alloy.

83. The composite device of claim 82, wherein said shape memory nickel-titanium alloy is heat treated such that the alloy is highly flexible at a temperature appropriate for introduction into the body via a catheter, and after placement, the device will take on a shape designed to optimize the therapeutic purposes desired for the device.

84. The composite device of claim 73, wherein said shape memory material comprises a shape memory polymer.

85. The composite device of claim 73, wherein at least one of the strands comprises a metal wire selected from the group consisting of copper and copper alloys or other metal alloys.

86. The composite device of claim 73 wherein at least one strand comprises a fiber selected from the group consisting of polyester, polyglycolic acid, polylactic acid, fluoropolymers, nylons, polyaramid fiber and silk chosen for thrombogenicity.

87. The composite device of claim 86, wherein said fiber is wound into said cable so that said fiber projects beyond the diameter of the other strands in said cable.

88. The composite device of claim 73, wherein at least one of the strands comprises a therapeutic agent selected from the group consisting of human growth hormone; genetic material; antigens; hydrogels; a metal wire selected from the group consisting of copper and copper alloys; and a fiber selected from the group consisting of polyester, polyglycolic acid, polylactic acid, fluoropolymers, nylons, polyaramid fiber and silk chosen for thrombogenicity.

89. The composite device of claim 88, wherein at least one of the strands is impregnated with said therapeutic agent.

90. The composite device of claim 86, wherein at least one of the strands is coated with said therapeutic agent.

91. The composite device of claim 86, wherein said therapeutic agent is disposed axially in a central core of said composite device.

92. The composite device of claim 73, wherein at least one of the strands comprises a therapeutic agent including at least one component selected from the group consisting of hydrogel, collagen, and bio-absorbable polymers including lactic acids, glycolic acids and caprolactam.

93. The composite device of claim 73, further comprising means to conduct energy.

94. The composite device of claim 93, wherein said means to conduct energy comprises an optical fiber to conduct light energy.

95. The composite device of claim 93, wherein said means to conduct energy comprises means to conduct electrical energy.

96. The composite device of claim 73, wherein said plurality of strands comprises a plurality of exterior strands surrounding at least one interior strand.

97. The composite device of claim 73, wherein said plurality of strands comprises a plurality of exterior strands surrounding a central core of said composite device.

98. The composite device of claim 73, wherein said radiopaque strand comprises at least one centrally, axially disposed radiopaque wire, and said radiopaque wire is formed from a metal selected from the group consisting of platinum, tungsten, and gold.

99. The composite device of claim 73, wherein said outer cover comprises a sheath to constrain said strands of said micro-cable about a longitudinal axis.

100. The composite device of claim 99, wherein said sheath comprises a containment strand wound about said longitudinal strands.

101. The composite device of claim 100, wherein said containment strand is wound at varying intervals along the outside to provide variations in the torqueability and stiffness of the composite cable.

102. The composite device of claim 100, wherein the width of the outer cover is varied along the composite cable.

103. The composite device of claim 99, wherein said sheath comprises a plurality of heat shrink plastic tubes placed to provide bending stiffness in said cable which varies with the position on said cable.

104. The composite device of claim 99, wherein outer cover comprises a plurality of layers formed of different materials in order to provide a graduated bending and stiffness characteristic over the length of the cable.

105. The composite device of claim 73, wherein said outer cover comprises an outer sheath of material to provide bending stiffness and constrain said longitudinal strands about said longitudinal axis, said sheath being formed of a low friction material selected from the group consisting of a fluoropolymer and a heat shrinkable plastic tube.

106. The composite device of claim 73, wherein said strands of the micro-cable are bundled by a plurality of bands disposed at intervals along said micro-cable to produce a composite banded cable.

107. The composite device of claim 106, wherein said strands are laid parallel within the composite banded cable.

108. The composite device of claim 106, wherein said strands are twisted within the composite banded cable.

109. The composite device of claim 106, wherein composite cable comprises a single inner micro-cable.

110. The composite device of claim 73, wherein said outer cover varies in cross section along its length to provide bending stiffness of said composite cable which varies along said composite cable.

111. The composite device of claim 73, wherein the number of strands and the degree to which they extend along said composite cable within the outer cover varies along said composite cable.

112. The composite device of claim 73, wherein said multi-stranded micro-cable is approximately 0.0021 to 0.0045 inches in diameter.

113. The composite device of claim 73, wherein said composite microcable comprises a plurality of micro-cables disposed within said outer cover in order to provide desired bending and strength characteristics.

114. The composite device of claim 113, wherein said plurality of micro-cables are helically wound within said outer cover.

115. The composite device of claim 113, wherein said plurality of micro-cables extend parallel and longitudinally within said outer cover.

116. The composite device of claim 113, wherein said composite cable has a collapsed primary configuration and an expanded secondary configuration with a secondary three dimensional shape selected from the group consisting of spherical, helical and conical shapes.

117. The composite device of claim 113, wherein said plurality of micro-cables are bundled by at least one outer cover to produce said composite banded cable.

118. The composite device of claim 113, wherein said plurality of micro-cables are banded at intervals by a plurality of bands.

119. The composite device of claim 73, further comprising at least one longitudinal element for sensing a parameter selected from the group consisting of an optical imaging element, an optical fiber, a thermal imaging element, and an ultrasound imaging element.

120. A three dimensional composite device having a collapsed coil configuration with a primary shape and an expanded coil configuration with a secondary three dimensional shape for use in interventional therapy and vascular surgery, the device adapted to be inserted into a portion of a vasculature for occluding the portion of the vasculature, comprising:
a plurality of multi-stranded micro-cables having a collapsed coil configuration with a primary shape and an expanded coil configuration with a secondary three dimensional shape, each said multi-stranded micro-cable having a plurality of flexible strands of a shape memory material, and at least one said strand being a radiopaque strand to provide a radiopaque marker of the deployed configuration of a device made of the cable during vascular surgery.

121. The device of claim 120, said micro-cable further comprising at least one outer cover disposed over at least a portion of said plurality of multi-stranded micro-cables to produce a composite banded cable.

122. The three dimensional composite device of claim 121, wherein said secondary three dimensional shape is selected from the group consisting of generally spherical, generally helical, and generally conical shapes.

123. The three dimensional composite device of claim 121, wherein said plurality of strands are helically wound.

124. The three dimensional composite device of claim 121, wherein said plurality of flexible strands are parallel longitudinal strands.

125. The three dimensional composite device of claim 121, wherein at least one of said plurality of strands comprises a super-elastic material.

126. The three dimensional composite device of claim 125, wherein said super-elastic material comprises a nickel titanium alloy.

127. The three dimensional composite device of claim 121, wherein a plurality of said flexible strands are comprised of a super-elastic material.

128. The three demensional composite device of claim 121, wherein at least one of the strands comprises a therapeutic agent selected from the group consisting of human growth hormone; genetic material; antigens; hydrogels; a metal wire selected from the group consisting of copper and copper alloys; and a fiber selected from the group consisting of polyester, polyglycolic acid, polylactic acid, fluoropolymers, nylons, polyaramid fiber and silk chosen for thrombogenicity.

129. The device of claim 128, wherein at least a portion of said strand of therapeutic agent projects beyond the diameter of the remaining strands on said cable.

130. The three dimensional composite device of claim 128, wherein at least one of the strands is impregnated with said therapeutic agent.

131. The three dimensional composite device of claim 128, wherein at least one of the strands is coated with said therapeutic agent.

132. The three dimensional composite device of claim 128, wherein said therapeutic agent is disposed axially in a central core of said three dimensional composite device.

133. The three dimensional composite device of claim 121, wherein at least one of said strands comprises a therapeutic agent including at least one component selected from the group consisting of hydrogel, collagen, and bioabsorbable polymers including lactic acids, glycolic acids and caprolactam.

134. The three dimensional composite device of claim 121, further comprising means to conduct energy.

135. The three dimensional composite device of claim 134, wherein said means to conduct energy comprises an optical fiber to conduct light energy.

136. The three dimensional composite device of claim 121, wherein said plurality of strands comprises a plurality of exterior strands surrounding at least one interior strand.

137. The three dimensional composite device of claim 121, wherein said plurality of strands comprises a plurality of exterior strands surrounding a central core of said three dimensional composite device.

138. The three dimensional composite device of claim 121, wherein said radiopaque strand comprises at least one centrally, axially disposed radiopaque wire, and said radiopaque wire is formed from a metal selected from the group consisting of platinum, tungsten, and gold.

139. The three dimensional composite device of claim 121, wherein said outer cover comprises a sheath to constrain said strands of said micro-cable about a longitudinal axis.

140. The three dimensional composite device of claim 139, wherein said sheath comprises a containment strand wound about said longitudinal strands.

141. The three dimensional composite device of claim 140, wherein said containment strand is wound at varying intervals along the outside to provide variations in the torqueability and stiffness of the composite cable.

142. The three dimensional composite device of claim 140, wherein the width of the outer cover is varied along the composite cable.

143. The three dimensional composite device of claim 139, wherein said sheath comprises a plurality of heat shrink plastic tubes placed to provide bending stiffness in said cable which varies with the position on said cable.

144. The three dimensional composite device of claim 121, wherein said outer cover comprises an outer sheath of material to provide bending stiffness and constrain said longitudinal strands about said longitudinal axis, said sheath being formed of a low friction material selected from the group consisting of a fluoropolymer and a heat shrinkable plastic tube.

145. The three dimensional composite device of claim 144, wherein outer cover comprises a plurality of layers formed of different materials in order to provide a graduated bending and stiffness characteristic over the length of the cable.

146. The three dimensional composite device of claim 121, wherein said strands of the micro-cable are bundled by a plurality of bands disposed at intervals along said micro-cable to produce a composite banded cable.

147. The three dimensional composite device of claim 146, wherein said strands are laid parallel within the composite banded cable.

148. The three dimensional composite device of claim 146, wherein said strands are twisted within the composite banded cable.

149. The three dimensional composite device of claim 146, wherein composite cable comprises a single inner micro-cable.

150. The three dimensional composite device of claim 121, wherein said outer cover varies in cross section along its length to provide bending stiffness of said composite cable which varies along said composite cable.

151. The three dimensional composite device of claim 121, wherein the number of strands and the degree to which they extend along said composite cable within the outer cover varies along said composite cable.

152. The three dimensional composite device of claim 121, wherein said multi-stranded micro-cable is approximately 0.0021 to 0.0045 inches in diameter.

153. The three dimensional composite device of claim 121, wherein said composite microcable comprises a plurality of micro-cables disposed within said outer cover in order to provide desired bending and strength characteristics.

154. The three dimensional composite device of claim 153, wherein said plurality of micro-cables are helically wound within said outer cover.

155. The three dimensional composite device of claim 153, wherein said plurality of micro-cables extend parallel and longitudinally within said outer cover.

156. The three dimensional composite device of claim 153, wherein said composite cable has a collapsed primary configuration and an expanded secondary configuration with a secondary three dimensional shape selected from the group consisting of spherical, helical and conical shapes.

157. The three dimensional composite device of claim 153, wherein said plurality of micro-cables are bundled by at least one outer cover to produce said composite banded cable.

158. The three dimensional composite device of claim 153, wherein said plurality of micro-cables are banded at intervals by a plurality of bands.

159. The three dimensional composite device of claim 121, further comprising at least one longitudinal element for sensing a parameter selected from the group consisting of an optical imaging element, an optical fiber, a thermal imaging element, and an ultrasound imaging element.

160. The three dimensional composite device of claim 120, wherein said shape memory material comprises a nickel-titanium alloy.

161. The three dimensional composite device of claim 160, wherein said shape memory nickel-titanium alloy is heat treated such that the alloy is highly flexible at a temperature appropriate for introduction into the body via a catheter, and after placement, the device will take on a shape designed to optimize the therapeutic purposes desired for the device.

162. The three dimensional composite device of claim 120, wherein said shape memory material comprises a shape memory polymer.

163. A composite micro-cable for use in interventional therapy comprising:
   at least one longitudinal strand made of a radiopaque material;
   at least one longitudinal strand made of a flexible shape memory material; and
   at least one strand of a therapeutic material which extends beyond the diameter of the other strands in the micro-cable along the length of the cable.

* * * * *

UNITED STATES PATENT AND TRADEMARK OFFICE
CERTIFICATE OF CORRECTION

PATENT NO. : 6,159,165
DATED : December 12, 2000
INVENTOR(S) : David A. Ferrera, Christopher G. M. Ken It is certified that error appears in the above-identified patent and that said Letters Patent is hereby corrected as shown below:

Title page,
Under OTHER DOCUMENTS, add the following:
-- " 'Mini' Gianturco Stainless Steel Coils for Transvascular Occlusion" by James H. Anderson, et al., from the Department of Diagnostic Radiology at the University of Texas System Cancer Center, August 1978, pp. 301-303.
"A New Improved Coil for Tappered-Tip Catheter for Arterial occlustion" by Vincent P. Chuang, M.D., et al., May 1980, pp. 505-509. --.

Column 14, claim 21,
Line 41, change "15", to read -- 13 --.

Column 17, claim 90,
Line 36, change "86", to read -- 88 --.

Column 17, claim 91,
Line 38, change "86", to read -- 88 --.

Column 19, claim 126,
Line 36, change "125", to read -- 121 --.

Signed and Sealed this

Twenty-seventh Day of November, 2001

*Attest:*

NICHOLAS P. GODICI
*Attesting Officer*     *Acting Director of the United States Patent and Trademark Office*